(12) United States Patent
Heiser et al.

(10) Patent No.: US 7,608,577 B2
(45) Date of Patent: Oct. 27, 2009

(54) PEPTIDYL KETONES AS INHIBITORS OF DPIV

(75) Inventors: Ulrich Heiser, Haale/Saale (DE); André Johannes Niestroj, Sennewitz (DE); Torsten Hoffmann, Haale/Saale (DE); Hans-Ulrich Demuth, Haale/Saale (DE)

(73) Assignee: OSI Pharmaceuticals, Inc., Melville, NY (US)

( * ) Notice: Subject to any disclaimer, the term of this patent is extended or adjusted under 35 U.S.C. 154(b) by 483 days.

(21) Appl. No.: 10/216,305

(22) Filed: Aug. 9, 2002

(65) Prior Publication Data

US 2003/0148961 A1    Aug. 7, 2003

Related U.S. Application Data

(60) Provisional application No. 60/340,151, filed on Dec. 14, 2001.

(30) Foreign Application Priority Data

Oct. 12, 2001    (DE) ................. 101 50 203

(51) Int. Cl.
A61K 38/00 (2006.01)
C07K 2/00 (2006.01)
C07K 1/02 (2006.01)
C07K 1/107 (2006.01)

(52) U.S. Cl. ............... 514/2; 530/300; 530/333; 530/345

(58) Field of Classification Search ......... 530/300, 530/331, 332, 345; 420/335; 514/2
See application file for complete search history.

(56) References Cited

U.S. PATENT DOCUMENTS

| 2,961,377 | A |   | 11/1960 | Shapiro et al. ........ 167/65 |
| 3,174,901 | A |   | 3/1965 | Sterne ........... 167/65 |
| 3,879,541 | A |   | 4/1975 | Kabbe et al. ......... 424/326 |
| 3,960,949 | A |   | 6/1976 | Ahrens et al. ....... 260/564 B |
| 4,028,402 | A |   | 6/1977 | Fischer et al. ....... 260/501.14 |
| 4,643,991 | A | * | 2/1987 | Digenis et al. ........ 514/18 |
| 4,935,493 | A |   | 6/1990 | Bachovchin et al. ...... 530/331 |
| 5,008,245 | A | * | 4/1991 | Digenis et al. ........ 514/18 |
| 5,162,307 | A | * | 11/1992 | Digenis et al. ....... 514/18 |
| 5,433,955 | A |   | 7/1995 | Bredehorst et al. ....... 424/94.3 |
| 5,462,928 | A |   | 10/1995 | Bachovchin et al. ....... 514/19 |
| 5,512,549 | A |   | 4/1996 | Chen et al. .......... 514/12 |
| 5,543,396 | A |   | 8/1996 | Powers et al. ........ 514/19 |
| 5,614,379 | A |   | 3/1997 | MacKellar .......... 435/68.1 |
| 5,624,894 | A |   | 4/1997 | Bodor ............ 514/2 |
| 5,639,783 | A | * | 6/1997 | Ando et al. ......... 514/456 |
| 5,834,508 | A | * | 11/1998 | Ando et al. ......... 514/471 |
| 5,922,319 | A | * | 7/1999 | Digenis et al. ........ 424/94.64 |
| 5,939,560 | A |   | 8/1999 | Jenkins et al. ........ 548/535 |
| 6,006,753 | A |   | 12/1999 | Efendic ............ 128/898 |
| 6,319,893 | B1 |  | 11/2001 | Demuth et al. ........ 514/2 |

| 2001/0020006 | A1 | * | 9/2001 | Demuth et al. ......... 514/19 |

FOREIGN PATENT DOCUMENTS

| DE | 25 42 598 A1 | 4/1976 |
| DE | 296 075 A5 | 11/1991 |
| DE | 196 16 486 C2 | 10/1997 |
| DE | 299 09 210 U | 9/1999 |
| DE | 198 26 972 A1 | 12/1999 |
| EP | 0 658 568 A1 | 6/1995 |
| EP | 0 708 179 A2 | 4/1996 |
| FR | 2 085 665 | 12/1971 |
| FR | 2 696 740 A1 | 4/1994 |
| JP | 04-288098 | 10/1992 |
| JP | 4334357 | 11/1992 |
| WO | WO 91/11457 | 8/1991 |
| WO | WO 91/16339 | 10/1991 |
| WO | WO 91/17767 | 11/1991 |
| WO | WO 93/08259 | 4/1993 |
| WO | WO 95/11689 | 5/1995 |
| WO | WO 95/15309 | 6/1995 |
| WO | WO 95/29691 | 11/1995 |
| WO | WO 97/40832 | 11/1997 |
| WO | WO 97/45117 | 12/1997 |
| WO | WO 98/19998 | 5/1998 |
| WO | WO 98/22494 | 5/1998 |
| WO | WO 99/46272 A | 9/1999 |
| WO | PCT/EP99/04381 | * 12/1999 | .......... 514/19 |
| WO | WO 99/62914 | 12/1999 |
| WO | WO 00/01849 | 1/2000 |
| WO | WO 00/10549 | 3/2000 |
| WO | WO 00/53171 | 9/2000 |

(Continued)

OTHER PUBLICATIONS

S Tsutsumi, et al. Synthesis and structure-activity relationships of peptidyl alpha-keto heterocycles as novel inhibitors of prolyl endopeptidase. (1994) J. Med. Chem. 37, 3492-3502.*

(Continued)

Primary Examiner—Andrew D Kosar

(57) ABSTRACT

The present invention relates to compounds of the general formula 1

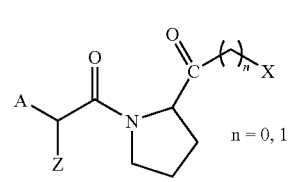

and pharmaceutically acceptable salts thereof, to the use of the compounds for the treatment of impaired glucose tolerance, glucosuria, hyperlipidaemia, metabolic acidosis, diabetes mellitus, diabetic neuropathy and nephropathy and of sequelae caused by diabetes mellitus in mammals.

5 Claims, No Drawings

FOREIGN PATENT DOCUMENTS

| WO | WO 01/34594 A1 | 5/2001 |
|---|---|---|
| WO | WO 01/62266 | 8/2001 |
| WO | WO 01/74299 A2 | 10/2001 |
| WO | WO 01/89569 A1 | 11/2001 |
| WO | WO 01/97808 | 12/2001 |
| WO | WO 02/20825 A1 | 3/2002 |

OTHER PUBLICATIONS

P. Walther and W. Grondler. Studia Biophysica (1983) 96(3), pp. 235-236.*
Fittkau, et al. Biomedica Biochmica Acta (1984) 43(7), pp. 887-899.*
S. Fittkau, et al. Biomed. Biochim. Acta (1984) 43(7), pp. 887-899. English Translation, 26 pages.*
F. Rypacek, et al. J. Med. Chem. (1994) 37, pp. 1850-1856.*
M. Kato et al. J. Enzyme Inhibition. (1993) 7, pp. 105-130.*
R. Joyeau et al. Eur. J. Med. Chem. (2000) 35, pp. 257-266.*
Campbell, I.W. *New Antidiabetic Drugs*, ed. C.J. Bailey & P.R. Flatt, Smith-Gordon, "Sulphonylureas and metformin: efficacy and inadequacy". 3:33-51 (1990).
The Merck Index, 11th Edition, *An Encyclopedia of Chemicals. Drugs*, and Biologicals, 1989, p. 934.
The Merck Index, 12th Edition, *An Encyclopedia of Chemicals, Drugs*, and Biologicals, 1996, p. 1014.
*Martindale The Extra Pharmacopoeia*, 30th Edition, London Pharmaceutical Press, 1993, p. 1619.
*Martindale The Extra Pharmacopoeia*, 30th Edition, London Pharmaceutical Press, 1993, p. 36.
*Chemical Abstracts*, vol. 115. No. 15, Oct. 14, 1991 Columbus, Ohio, US; abstract No. 149947q, Schoen Ekkehard et al: "Dipeptidyl peptidase IV in the immune system. Effects of specific enzyme inhibitors on activity of dipeptidyl peptidase IV and proliferation of human lymphocytes".
*Chemical Abstracts*, vol. 126, No. 2, Jan. 13, 1997 Columbus, Ohio, US; abstract No. 16161j, Stoeckel A. et al: "Competitive inhibition of proline specific enzymes by amino acid thioxopyrrolidides and thiazolidides".
*Chemical Abstracts*, vol. 118, No. 25, Jun. 21, 1993 Columbus, Ohio, US; abstract No. 255342k, Hosoda, et al, "Preparation of N-(heterocyclic Carbonyl) Amino Acids and Analogs as Prolyl Endopeptidase Inhibitors", (Nov. 20, 1992).
Arai et al., "Synthesis of prolyl endopeptidase inhibitors and evaluation of their structure-activity relationships : in vitro inhibition of prolyl endopeptidase from Canine Brain" *Chemical and Pharmaceutical Bulletin*., Bd. 41, No. 9, 1993, pp. 1583-1588.
J. Lin et al.: "Inhibition of depeptidyl peptidase IV by fluoroolefin-containing n-peptidyl-O-hydroxylamine peptidomimetics" *Proceedings of the National Academy of Sciences of USA*, vol. 95, Nov. 1998, pp. 14020-14024.
Korom, S., et al "Inhibition of CD26/dipeptidyl peptidase IV activity in vivo prolongs cardiac allograft survival in rat recipients", Transplantation, vol. 63, 1495-1500 No. 10 (1997).
Tanka, S., et al., "Suppression of arthritis by the inhibitors of dipeptidyl peptidase IV". *Int. J. Immunopharmacol*, vol. 19, No. 1 pp. 15-24, (1997).
Mentlein, R., et al., "Proteolytic processing of neuropeptide Y and peptide YY by dipeptidyl peptidase IV". *Regul. Pept.* 49, 133-144 (1993).
Wetzel, W., et al., "Effects of the CLIP fragment ACTH 20-24 on the duration of REM sleep episodes". *Neuropeptides*, 31, 41-45 (1997).
Amasheh, S., et al., "Electrophysiological analysis of the function of the mammalian renal peptide transporter expressed in Xenopus Laevis oocytes". *J. Physiol.* 504, 169-174 (1997).
Durinx, C.; et al.; "Reference Values for Plasma Dipeptidyl-Pepidase IV activity and their Association with Other Laboratory Parameters". *Clin Chem Lab Med 2001*, February; 39 (2) :155-9, 1 page, Abstract Only.
Gossrau, R.; "Cytochemistry of Membrane Proteases". *Histochem J*, Jul. 1985; 17 (7) :737-71, 1 page, Abstract Only.

Hahn, T.; et al.; "Enzyme Histochemical Evidence for the Presence of Potential Blood Regulating Proteases in Cultured Villous Explants from Human First Trimester Placentae". *Acta Histochem* Dec. 1993, 95 (2) :185-92, 1 page, Abstract Only.
Heymann, E. et al., "Has Dipeptidyl Peptidase IV an Effect on Blood Pressure and Coagulation." *Klin Wochenscher*, Jan. 1984, 2;62 (1) :2-10, 1 page, Abstract Only.
Magyar, C.E. et al., "Proximal Tubule Na Transporter Responses are the same during Acute and Chronic Hypertension." *Am J. Physiol Renal Physiol*, Aug. 2000; 279 (2) :F358-69, 1 page, Abstract Only.
Papies, B. et al., "Isoenzyme (Lactate Dehydrogenase, Aspartate Aminotransferase) and Dipeptidyl Peptidase IV Activity Changes in Blood Plasma Likely Indicative of Organ Involvement due to Arterial Hypertension." *Cor Vasa*, 1991; 33 (3) :218-26, 1 page, Abstract Only.
Qureshi. N.U.; et al., "Endogenous Neuropeptide Y Mediates Vasoconstriction during Endotoxic and Hemorrhagic Shock". *Regul Pept*, Sep. 25, 1998; 75-76:215-20, 1 page, Abstract Only.
Index Nominum, *International Drug Directory 1992/1993*, Medpharm Scientific Publishers, pp. 728-729.
The Merck Index, *An Encyclopedia of Chemicals and Drugs*, 9th Edition, Merck & Co., Inc., 1976, p. 773.
Willms et al., Journal of Clinical Endocrinology Metabolism, "Gastric Emptying, Glucose Responses, and Insulin Secretion after a Liquid Test Meal: Effects of Exogenous Glucagon-Like Peptide-1 (GLP-1)-(7-36) Amide in Type 2 (Noninsulin-Dependent) Diabetic Patients", 1996, 81(1): 327-332.
Hoffmann et al., *Journal of Chromatography A*, "Inhibition of dipeptidyl peptidase IV (DP IV) by anti-DP IV antibodies and non-substrate X-X-Pro- oligopeptides ascertained by capillary eletrophoresis", 1995, 716:355-362.
C.B. Welch, *Medical Management of Non-Insulin-Dependent (Type II) Diabetes*, 3rd edition, American Diabetes Association, "Diagnosis and Classification" p. 3, 1994, Pharmacologic Intervention (2 pages).
Mannucci et al., *Diabetes Care*, "Effect of Metformin on Glucagon-Like Peptide 1 (GLP-1) and Leptin Levels in Obese Nondiabetic Subjects", 24(3): 489-494, Mar. 2001.
Stryer, *Biochemistry 3rd Ed.*, "Protein Conformation, Dynamics, and Function", 1988, p. 191-193.
Pauly et al., *Regulatory Peptides*, "Abstracts Issue: Abstracts from the 11th International Symposium on Regulatory Peptides", Jul. 15, 1996, 64(1-3): 148 plus cover.
Gutniak et al., *New England Journal of Medicine*, "Antidiabetogenic Effect of Glucagon-like peptide-1 (7-36) Amide in Normal Subjects and Patients With Diabetes Mellitus", 1992, 326: 1316-1322.
Hendrick et al., *Metabolism—Clinical and Experimental*, "Glucagon-like Peptide-I-(7-37) Suppresses Hyperglycemia in Rats", Jan. 1993, 42(1):1-6.
Nauck et al., *Diabetologia*, "Normalization of fasting hyperglycaemia by exogenous glucagon-like peptide 1 (7-36 amide) in Type 2 (non-insulin-dependent) diabetic patients", (1993), 36: 741-744.
Gutniak et al., *Diabetes Care*, "Subcutaneous Injection of the Incretin Hormone Glucagon-Like Peptide 1 Abolishes Postprandial Glycemia in NIDDM", Sep. 1994, 17(9): 1039-1044.
Deacon et al., *Journal of Clinical Endocrinology and Metabolism*, "Degradation or Glucagon-Like Peptide-1 by Human Plasma in Vitro Yields and N-Terminally Truncated Peptide That Is a Major Endogenous Metabolite in Vivo", (1995), 80(3): 952-957.
H.A. Smith et al., *Veterinary Pathology* (fourth edition), "Diseases and Disorders of Metabolism: Deficiency Diseases", (1972), p. 1018-1020.
G.G. Duncan, *Diseases of Metabolism (Asian edition)*, "Diabetes Mellitus", (1966), p. 951-957.
T.J. Kieffer et al., "Degradation of Glucose-Dependent Insulinotropic Polypetide and Truncated Glucagon-Like Peptide 1 in Vitro and In Vivo by DP IV", *Endocrinology*, vol. 136(8), (1995), p. 3585-3596.
C.F. Deacon et al., *Diabetes*, "Both Subcutaneously and Intravenously Administered Glucagon-Like Peptide I Are Rapidly Degraded from the $NH_2$-Terminus in Type II Diabetic Patients and in Healthy Subjects", Sep. 1995, 44: 1126-1131.

Pauly et al., *Metabolism*, "Improved Glucose Tolerance in Rats Treated with the Dipeptidyl Peptidase IV (CD26) Inhibitor Ile-Thiazolidide", (1999), 48(3): 385-389.

*Goodman & Gilman's The Pharmacological Basis of Therapeutics*, Ninth Edition, (1996), p. 1510.

Nathan et al., *Diabetes Care*, "Insulinotropic Action of Glucagonlike Peptide-1-(7-37) in Diabetic and Nondiabetic Subjects", Feb. 1992, 15(2): 270-275.

Frohman et al., *Journal of Clin. Invest.*, "Rapid Enzymatic Degradation of Growth Hormone-releasing Hormone by Plasma in Vitro and in Vivo to a Biologically Inactive Product Cleaved at the $NH_2$ Terminus", vol. 78, Oct. 1986, p. 906-913.

Snow et al., *Advances In Medicinal Chemistry*, "Boronic Acid Inhibitors of Dipeptidyl Peptidase IV: A New Class of Immunosuppressive Agents", vol. 3, (1995), p. 149-177.

Thorens et al., *Diabetes*, "Glucagon-Like Pepetide-I and the Control of Insulin Secretion in the Normal State and in NIDDM", (1993), 42:1219-1225.

Wakselman et al., "Inhibition of HIV-1 infection of CD 26+ but not CD 26 cells by a potent cyclopeptidic inhibitor of the DPP IV activity of CD26", Abstract P 44 of the 24th *European Peptide Symposium*, (1996).

Ashworth et al., *Bioorg. Med. Chem. Lett.*, "2-Cyanopyrrolidides as Potent, Stable Inhibitors of Dipeptidyl Peptidase IV", (1996), 6(10): 1163-1166.

Endroczi et al., *ACTA Physiol. Hung.*, "Dipeptidyl peptidase IV (DP IV) and Superoxide Dismutase Activity in Thymus-Derived Lymphocytes: Effects of Inhibitory Pepdides and $Zn^{2+}$ in Vitro", (1990), 75(1): 35-44.

Lee, H.S. et al., "Cathepsin B Inhibitory Peptides Derived from β-Casein," *Peptides* 21 (2000) 807-809.

Edwards, J.V. et al., *J. Peptide Res.*, "Synthesis and Activity of $NH_2$-and COOH-Terminal Elastase Recognition Sequences on Cotton," (1999), 54: 536-543.

Wettstein, J.G. et al. *Pharmacology & Therapeutics*, "Central Nervous System Pharmacology of Neuropeptide Y.", (1995), 65(3): 397-414.

Badia-Elder N.E. et al., *Alcoholism Clinical and Experimental Research*, "Effects of Neuropeptide Y (NPY) on Ethanol Intake and Anxiety in High and Low Alcohol Drinking (HAD1/LAD1) Rats", (2000), 24(5): 82A.

Munglani R. et al., Drugs, *Adis International Ltd*, At, "The Therapeutic Potential of Neuropeptide Y Analgesic, Anxiolytic and Antihypertensive", (1996) 52(3): 371-389.

Reinhold, D. et al., *Journal of Neuroimmunology*, "Inhibitors of Dipeptidyl Peptidase IV/CD26 Suppress Activation of Human MBP-Specific CD4 + T Cell Clones", (1998) 87: 203-209.

Stöckel-Maschek, A., et al., *Biochimica et Biophysica Acta*, "Thioxo Amino Acid Pyrrolidides and Thiazolidides: new Inhibitors of Proline Specific Peptidases", (2000) 1479: 15-31.

*Vidal*, (1993), 69th Edition, p. 612-613.

*Pschyrembel*, Kininisches Wörterbuch 257, Auflage, (1994), 9 pages.

\* cited by examiner

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Synthetic peptide, C-terminal methylated, HBr
      salt

<400> SEQUENCE: 1

Val Pro Val Pro
1
```

PEPTIDYL KETONES AS INHIBITORS OF DPIV

RELATED APPLICATIONS

This application claims the benefit of priority to U.S. Provisional Patent Application No. 60/340,151 filed Dec. 14, 2001 and to German Patent Application DE 101 50 203 filed Oct. 12, 2001.

FIELD OF THE INVENTION

The present invention relates to peptidyl ketones and salts thereof, hereinafter referred to as peptidyl ketones, and to the use of the compounds for the preparation of a medicament for the in vivo inhibition of DPIV or/and DPIV-like enzymes.

The invention relates especially to the use of the compounds for the preparation of a medicament for the treatment of impaired glucose tolerance, glucosuria, hyperlipidaemia, metabolic acidosis, diabetes mellitus, diabetic neuropathy and nephropathy and of sequelae caused by diabetes mellitus in mammals, for the treatment of metabolism-related hypertension and of cardiovascular sequelae caused by hypertension in mammals, for the prophylaxis or treatment of skin diseases and diseases of the mucosae, autoimmune diseases and inflammatory conditions, and for the treatment of psychosomatic, neuropsychiatric and depressive illnesses, such as anxiety, depression, sleep disorders, chronic fatigue, schizophrenia, epilepsy, nutritional disorders, spasm and chronic pain.

BACKGROUND OF THE INVENTION

Dipeptidyl peptidase IV (DPIV) is a post-proline (to a lesser extent post-alanine, post-serine or post-glycine) cleaving serine protease found in various tissues of the body including kidney, liver, and intestine, where it removes dipeptides from the N-terminus of biologically active peptides with a high specificity when proline or alanine form the residues that are adjacent to the N-terminal amino acid in their sequence.

The term DPIV-like enzymes relates to structurally and/or functionally DPIV/CD26-related enzyme proteins (Sedo & Malik, Dipeptidyl peptidase IV-like molecules: homologous proteins or homologous activities? Biochimica et Biophysica Acta 2001, 36506: 1-10). In essence, this small group of enzymes has evolved during evolution to release H-Xaa-Pro-Dipeptides and H-Xaa-Ala-Dipeptides from the N-terminus of oligo- or polypeptides. They show the common feature, that they accomodate in the Pro-position also Ala, Ser, Thr and other amino acids with small hydrophobic side-chains as Gly or Val. The hydrolytic efficacy is ranked Pro>Ala>>Ser, Thr>>Gly, Val. Same proteins have been only available in such small quantities that only the post-Pro or post-Ala cleavage could be established. While the proteins: DPIV, DP II, FAPα (Seprase), DP 6, DP 8 and DP 9 are structurally related and show a high sequence homology, attractin is an extraordinary functional DPIV-like enzyme, characterized by a similar activity and inhibitory pattern.

Further DPIV-like enzymes are disclosed in WO 01/19866, WO 02/34900 and WO02/31134. WO 01/19866 discloses novel human dipeptidyl aminopeptidase 8 (DPP8) with structural and functional similarities to DPIV and fibroblast activation protein (FAP). WO 02/34900 discloses a novel dipeptidyl peptidase 9 (DPP9) with significant homology to the amino acid sequences of DPIV and DPP8. WO 02/31134 discloses three DPIV-like enzymes, DPRP1, DPRP2 and DPRP3. Sequence analysis revealed that DPRP1 is identical to DPP8 as disclosed in WO 01/19866, that DPRP2 is identical to DPP9 and that DPRP3 is identical to KIAA1492 as disclosed in WO 02/04610.

Likewise, it has been discovered that DPIV is responsible for inactivating glucagon-like peptide-1 (GLP-1) and glucose-dependent insulinotropic peptide also known as gastric-inhibitory peptide (GIP). Since GLP-1 is a major stimulator of pancreatic insulin secretion and has direct beneficial effects on glucose disposal, in WO 97/40832 and U.S. Pat. No. 6,303,661 inhibition of DPIV and DPIV-like enzyme activity was shown to represent an attractive approach for treating non-insulin-dependent diabetes mellitus (NIDDM).

The reduction of such DP IV and DPIV-like enzyme activity for cleaving such sub-strates in vivo can serve to suppress undesirable enzyme activity effectively both under laboratory conditions and in pathological conditions of mammals. For example, Diabetes mellitus type II (also diabetes of old age) is based upon reduced insulin secretion or disturbances in receptor function which are founded inter alia upon proteolytically determined abnormalities in the concentration of the incretins.

Hyperglycaemia and its associated causes and sequelae (also Diabetes mellitus) are treated according to the current state of the art by administering insulin (for example material isolated from bovine pancreas or also material obtained by genetic engineering) to those affected, in various forms of administration. All of the previously known methods and also more modern methods are characterised by high expenditure on materials, high costs and often by crucial impairment of the patient's life quality. The classical method (daily i.v. insulin injection, customary since the thirties) treats the acute symptoms of the disease but leads, after prolonged use, to inter alia severe vascular changes (arteriosclerosis) and nerve damage.

It is known that DPIV-Inhibitors may be useful for the treatment of impaired glucose tolerance and diabetes mellitus (International Patent Application, Publication Number WO 99/61431, Pederson R A et al, Diabetes. 1998 August; 47 (8):1253-8 and Pauly R P et al, Metabolism 1999 March; 48 (3):385-9). In particular WO 99/61431 discloses DPIV-Inhibitors comprising an amino acid residue and a thiazolidine or pyrrolidine group, and salts thereof, especially L-threo-isoleucyl thiazolidine, L-allo-isoleucyl thiazolidine, L-threo-isoleucyl pyrrolidine, L-allo-isoleucyl thiazolidine, L-allo-isoleucyl pyrrolidine, and salts thereof.

Further examples of low molecular weight dipeptidyl peptidase IV inhibitors are agents such as tetrahydroisoquinolin-3-carboxamide derivatives, N-substituted 2-cyanopyrroles and -pyrrolidines, N-(N'-substituted glycyl)-2-cyanopyrrolidines, N-(substituted glycyl)-thiazolidines, N-(substituted glycyl)-4-cyanothiazolidines, amino-acyl-borono-prolyl-inhibitors and cyclopropyl-fused pyrrolidines. Inhibitors of dipeptidyl peptidase IV are described in U.S. Pat. Nos. 6,011,155; 6,107,317; 6,110,949; 6,124,305; 6,172,081; WO 99/61431, WO 99/67278, WO 99/67279, DE 198 34 591, WO 97/40832, DE 196 16 486 C 2, WO 98/19998, WO 00/07617, WO 99/38501, WO 99/46272, WO 99/38501, WO 01/68603, WO 01/40180, WO 01/81337, WO 01/81304, WO 01/55105, WO 02/02560 and WO 02/14271, the teachings of which are herein incorporated by reference in their entirety concerning these inhibitors, their uses, definition and their production.

More recently, the installation of subcutaneous depot implants (the insulin is released in metered amounts, and daily injections are unnecessary) and the implantation (transplantation) of intact Langerhans cells into the dysfunctional pancreas gland or other organs and tissues have been proposed. Such transplantation is complicated from a technical point of view, It furthermore represents risky surgical intervention in the recipient and, in the case of cell transplantation, also requires methods of suppressing or by-passing the immune system.

The problem of the invention is therefore to provide new compounds for the treatment of, for example, impaired glucose tolerance, glucosuria, hyperlipidaemia, metabolic acidosis, diabetes mellitus, diabetic neuropathy and nephropathy and of sequelae caused by diabetes mellitus in mammals, metabolism-related hypertension and cardiovascular sequelae caused by hypertension in mammals, for the prophylaxis or treatment of skin diseases and diseases of the mucosae, autoimmune diseases and inflammatory conditions, and for the treatment of psychosomatic, neuropsychiatric and depressive illnesses, such as anxiety, depression, sleep disorders, chronic fatigue, schizophrenia, epilepsy, nutritional disorders, spasm and chronic pain, and a simple method for the treatment of those diseases.

SUMMARY OF THE INVENTION

That problem is solved according to the invention by providing compounds of the general formula 1 and pharmaceutically acceptable salts thereof, including all stereoisomers:

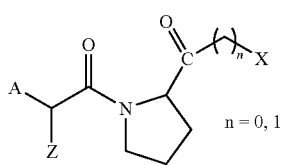

1 n = 0, 1 and pharmaceutically acceptable salts thereof, wherein:
A is selected from the following structures:

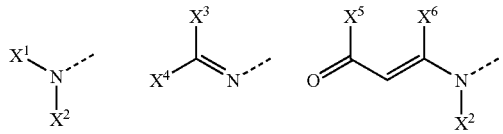

wherein
$X^1$ is H or an acyl or oxycarbonyl group including an amino acid residue, a N-protected amino acid residue, a peptide residue or a N-protected peptide residue,
$X^2$ is H, —(CH)$_m$—NH—C$_5$H$_3$N—Y with m=2-4 or —C$_5$H$_3$N—Y (a divalent pyridyl residue) and Y is selected from H, Br, Cl, I, NO$_2$ or CN,
$X^3$ is H or selected from an alkyl-, alkoxy-, halogen-, nitro-, cyano- or carboxy-substituted phenyl or from an alkyl-, alkoxy-, halogen-, nitro-, cyano- or carboxy-substituted pyridyl residue,
$X^4$ is H or selected from an alkyl-, alkoxy-, halogen-, nitro-, cyano- or carboxy-substituted phenyl or from an alkyl-, alkoxy-, halogen-, nitro-, cyano- or carboxy-substituted pyridyl residue,
$X^5$ is H or an alkyl, alkoxy or phenyl residue,
$X^6$ is H or an alkyl residue,
for n=1
X is selected from: H, OR$^2$, SR$^2$, NR$^2$R$^3$, N$^+$R$^2$R$^3$R$^4$, wherein:

$R^2$ stands for acyl residues, which are optionally substituted with alkyl, cycloalkyl, aryl or heteroaryl residues, or for amino acid residues or peptidic residues, or alkyl residues, which are optionally substituted with alkyl, cycloalkyl, aryl or heteroaryl residues,
$R^3$ stands for alkyl or acyl residues, wherein $R^2$ and $R^3$ may be part of a saturated or unsaturated carbocyclic or heterocyclic ring,
$R^4$ stands for alkyl residues, wherein $R^2$ and $R^4$ or $R^3$ and $R^4$ may be part of a saturated or unsaturated carbocyclic or heterocyclic ring,
for n=0
X is selected from:

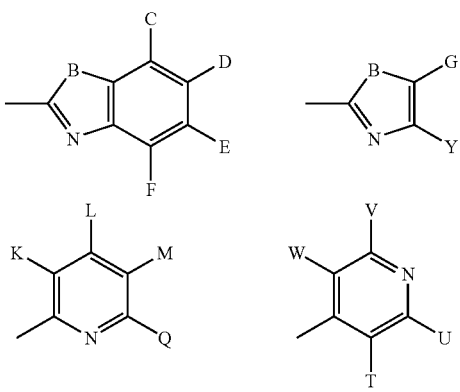

wherein
B stands for: O, S or NR$^5$, wherein R$^5$ is H, alkyl or acyl,
C, D, E, F, G, Y, K, L, M, Q, T, U, V and W are independently selected from alkyl and substituted alkyl residues, oxyalkyl, thioalkyl, aminoalkyl, carbonylalkyl, acyl, carbamoyl, aryl and heteroaryl residues, and
Z is selected from H, or a branched or straight chain alkyl residue from C$_1$-C$_9$, a branched or straight chain alkenyl residue from C$_2$-C$_9$, a cycloalkyl residue from C$_3$-C$_8$, a cycloalkenyl residue from C$_5$-C$_7$, an aryl or heteroaryl residue, or a side chain selected from all side chains of all natural amino acids or derivatives thereof.
In preferred compounds of formula 1, A is

wherein
$X^1$ is H or an acyl or oxycarbonyl group including an amino acid residue, N-acylated amino acid residue, a peptide residue from di- to pentapeptides, preferably a dipeptide residue, or a N-protected peptide residue from di- to pentapeptides, preferably a N-protected dipeptide residue,
$X^2$ is H, —(CH)$_m$—NH—C$_5$H$_3$N—Y with m=2-4 or —C$_5$H$_3$N—Y (a divalent pyridyl residue) and Y is selected from H, Br, Cl, I, NO$_2$ or CN,
for n=1
X is preferably selected from: H, OR$^2$, SR$^2$, NR$^2$R$^3$, wherein:
$R^2$ stands for acyl residues, which are optionally substituted with alkyl, cycloalkyl, aryl or heteroaryl residues, or for amino acid residues or peptidic residues, or alkyl residues, which are optionally substituted with alkyl, cycloalkyl, aryl or heteroaryl residues, R³ stands for alkyl or acyl residues, wherein R² and R³ may be part of a saturated or unsaturated carbocyclic or heterocyclic ring, for n=0

X is preferably selected from:

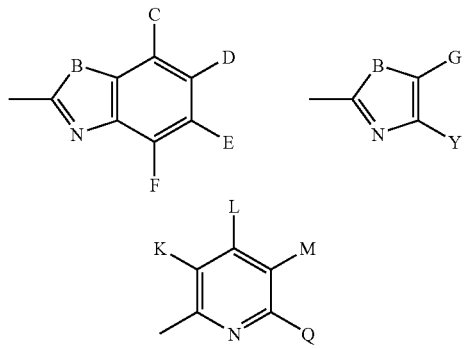

wherein

B stands for: O, S or NR⁵, wherein R⁵ is H, alkyl or acyl, C, D, E, F, G, Y, K, L, M and Q are independently selected from alkyl and substituted alkyl residues, oxyalkyl, thioalkyl, aminoalkyl, carbonylalkyl, acyl, carbamoyl, aryl and heteroaryl residues, and Z is selected from H, or a branched or straight chain alkyl residue from $C_1$-$C_9$, preferably $C_2$-$C_6$, a branched or straight chain alkenyl residue from $C_2$-$C_9$, a cycloalkyl residue from $C_3$-$C_8$, a cycloalkenyl residue from $C_5$-$C_7$, an aryl or heteroaryl residue, or a side chain selected from all side chains of all natural amino acids or derivatives thereof. In more preferred compounds of formula 1, A is

wherein

X¹ is H or an acyl or oxycarbonyl group including an amino acid residue, N-acylated amino acid residue or a peptide residue from di- to pentapeptides, preferably a dipeptide residue, or a N-protected peptide residue from di- to pentapeptides, preferably a N-protected dipeptide residue for n=1, X is preferably selected from: H, OR², SR², wherein:

R² stands for acyl residues, which are optionally substituted with alkyl or aryl residues, for n=0

X is preferably selected from:

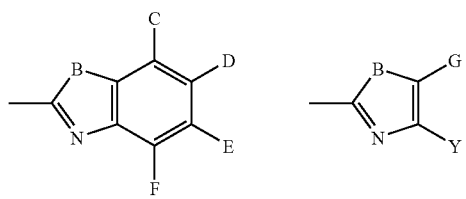

wherein

B stands for: O, S or NR⁵, wherein R⁵ is H, alkyl or acyl, C, D, E, F, G, Y, K, L, M and Q, are independently selected from alkyl and substituted alkyl residues, oxyalkyl, thioalkyl, aminoalkyl, carbonylalkyl, acyl, carbamoyl, aryl and heteroaryl residues, and Z is selected from H, or a branched or straight chain alkyl residue from $C_1$-$C_9$, preferably $C_2$-$C_6$, a branched or straight chain alkenyl residue from $C_2$-$C_9$, a cycloalkyl residue from $C_3$-$C_8$, a cycloalkenyl residue from $C_5$-$C_7$, an aryl or heteroaryl residue, or a side chain selected from all side chains of all natural amino acids or derivatives thereof. In most preferred compounds of formula 1, A is

wherein

X1 is H or an acyl or oxycarbonyl group including an amino acid residue, N-acylated amino acid residue or a dipeptide residue, containing a Pro or Ala in the penultimate position, or a N-protected dipeptide residue containing a Pro or Ala in the penultimate position, for n=1, X is H, for n=0

X is preferably selected from:

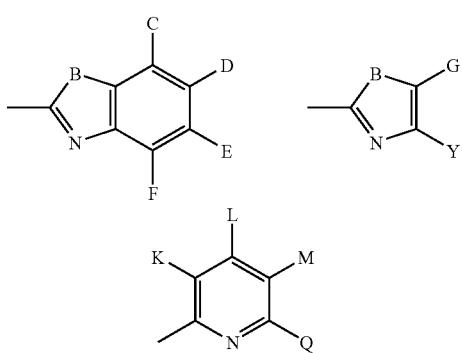

wherein

B stands for: O or S, most preferably for S

C, D, E, F, G, Y, K, L, M, Q, are H and

Z is selected from H, or a branched or straight chain alkyl residue from $C_3$-$C_5$, a branched or straight chain alkenyl residue from $C_2$-$C_9$, a cycloalkyl residue from $C_5$-$C_7$, a cycloalkenyl residue from $C_5$-$C_7$, an aryl or heteroaryl residue, or a side chain selected from all side chains of all natural amino acids or derivatives thereof.

Most preferred for Z is H.

According to a preferred embodiment the acyl groups are C1-C6-acyl groups.

According to a further preferred embodiment the alk(yl) groups are C1-C6-alk(yl) groups, which may be branched or unbranched.

According to a further preferred embodiment the alkoxy groups are C1-C6-alkoxy groups.

According to a further preferred embodiment the aryl residues are C5-C12 aryl residues that have optionally fused rings.

According to a further preferred embodiment the cycloalkyl residues (carbocycles) are C3-C8-cycloalkyl residues, According to a further preferred embodiment the heteroaryl residues are C4-C11 aryl residues that have optionally fused rings and, in at least one ring, additionally from 1 to 4 preferably 1 or 2 hetero atoms, such as O, N and/or S.

According to a further preferred embodiment peptide residues are corresponding residues containing from 2 to 50 amino acids.

According to a further preferred embodiment the heterocyclic residues are C2-C7-cycloalkyl radicals that additionally have from 1 to 4, preferably 1 or 2 hetero atoms, such as O, N and/or S.

According to a further preferred embodiment the carboxy groups are C1-C6 carboxy groups, which may be branched or unbranched.

According to a further preferred embodiment the oxycarbonyl groups are groups of the formula —O—$(CH_2)_{1-6}$COOH, The amino acids can be any natural or synthetic amino acid, preferably natural alpha amino acids.

Examples of amino acids which can be used in the present invention are L and D-amino acids, N-methyl-amino-acids; allo- and threo-forms of Ile and Thr, which can, e.g. be α-, β- or ω-amino acids, whereof α-amino acids are preferred.

Examples of amino acids are:

aspartic acid (Asp), glutamic acid (Glu), arginine (Arg), lysine (Lys), histidine (His), glycine (Gly), serine (Ser) and cysteine (Cys), threonine (Thr), asparagine (Asn), glutamine (Gln), tyrosine (Tyr), alanine (Ala), proline (Pro), valine (Val), isoleucine (Ile), leucine (Leu), methionine (Met), phenylalanine (Phe), tryptophan (Trp), hydroxyproline (Hyp), beta-alanine (beta-Ala), 2-amino octanoic acid (Aoa), azetidine-(2)-carboxylic acid (Ace), pipecolic acid (Pip), 3-amino propionic, 4-amino butyric and so forth, alpha-aminoisobutyric acid (Aib), sarcosine (Sar), omithine (Orn), citrulline (Cit), homoarginine (Har), t-butylalanine (t-butyl-Ala), t-butylglycine (t-butyl-Gly), N-methylisoleucine (N-MeIle), phenylglycine (Phg), cyclohexylalanine (Cha), norleucine (Nle), cysteic acid (Cya) and methionine sulfoxide (MSO), Acetyl-Lys, modified amino acids such as phosphoryl-serine (Ser(P)), benzyl-serine (Ser(Bzl)) and phosphoryl-tyrosine (Tyr(P)), 2-aminobutyric acid (Abu), aminoethylcysteine (AECys), carboxymethylcysteine (Cmc), dehydroalanine (Dha), dehydroamino-2-butyric acid (Dhb), carboxyglutaminic acid (Gla), homoserine (Hse), hydroxylysine (Hyl), cis-hydroxyproline (cisHyp), trans-hydroxyproline (transHyp), isovaline (Iva), pyroglutamic acid (Pyr), norvaline (Nva), 2-aminobenzoic acid (2-Abz), 3-aminobenzoic acid (3-Abz), 4-aminobenzoic acid (4-Abz), 4-(aminomethyl)benzoic acid (Amb), 4-(aminomethyl)cyclohexanecarboxylic acid (4-Amc), Penicillamine (Pen), 2-amino-4-cyanobutyric acid (Cba), cycloalkane-carboxylic acids.

Examples of v-amino acids are e.g.: 5-Ara (aminoraleric acid), 6-Ahx (aminohexanoic acid), 8-Aoc (aminooctanoic acid), 9-Anc (aminovanoic acid), 10-Adc (aminodecanoic acid), 11-Aun (aminoundecanoic acid), 12-Ado (aminododecanoic acid).

Further amino acids are: indanyglycine (Igl), indoline-2-carboxylic acid (Idc), octahydroindole-2-carboxylic acid (Oic), diaminopropionic acid (Dpr), diaminobutyric acid (Dbu), naphthylalanine (1-Nal), (2-Nal), 4-aminophenylalanine (Phe(4-$NH_2$)), 4-benzoylphenylalanine (Bpa), diphenylalanine (Dip), 4-bromophenylalanine (Phe(4-Br)), 2-chlorophenylalanine (Phe(2-Cl)), 3-chlorophenylalanine (Phe(3-Cl)), 4-chlorophenylalanine (Phe(4-Cl)), 3,4-chlorophenylalanine (Phe(3,4-$Cl_2$)), 3-fluorophenylalanine (Phe(3-F)), 4-fluorophenylalanine (Phe(4-F)), 3,4-fluorophenylalanine (Phe(3,4-$F_2$)), pentafluorophenylalanine (Phe($F_5$)), 4-guanidinophenylalanine (Phe(4-guanidino)), homophenylalanine (hPhe), 3-iodophenylalanine (Phe(3-I)), 4-iodophenylalanine (Phe(4-I)), 4-methylphenylalanine (Phe (4-Me)), 4-nitrophenylalanine (Phe-(4-$NO_2$)), biphenylalanine (Bip), 4-phosphonomethylphenylalanine (Pmp), cyclohexylglycine (Ghg), 3-pyridinylalanine (3-Pal), 4-pyridinylalanine (4-Pal), 3,4-dehydroproline (A-Pro), 4-ketoproline (Pro(4-keto)), thioproline (Thz), isonipecotic acid (Inp), 1,2,3,4,-tetrahydroisoquinolin-3-carboxylic acid (Tic), propargylglycine (Pra), 6-hydroxynorleucine (NU(6-OH)), homotyrosine (hTyr), 3-iodotyrosine (Tyr(3-I)), 3,5-diiodotyrosine (Tyr(3,5-$I_2$)), d-methyl-tyrosine (Tyr(Me)), 3-$NO_2$-tyrosine (Tyr(3-$NO_2$)), phosphotyrosine (Tyr($PO_3H_2$)), alkylglycine, 1-aminoindane-1-carboxy acid, 2-aminoindane-2-carboxy acid (Aic), 4-amino-methylpyrrol-2-carboxylic acid (Py), 4-amino-pyrrolidine-2-carboxylic acid (Abpc), 2-aminotetraline-2-carboxylic acid (Atc), diaminoacetic acid (Gly($NH_2$)), diaminobutyric acid (Dab), 1,3-dihydro-2H-isoinole-carboxylic acid (Disc), homocyclohexylalanine (hCha), homophenylalanine (hPhe Hof), trans-3-phenyl-azetidine-2-carboxylic acid, 4-phenyl-pyrrolidine-2-carboxylic acid, 5-phenyl-pyrrolidine-2-carboxylic acid, 3-pyridylalanine (3-Pya), 4-pyridylalanine (4-Pya), styrylalanine, tetrahydroisoquinoline-1-carboxylic acid (Tiq), 1,2,3, 4-tetrahydronorharmane-3-carboxylic acid (Tpi), β-(2-thienyl)-alanine (Tha).

Upon—preferably oral—administration of those compounds to a mammal, the endogenous (or additionally exogenously administered) insulinotropic peptides $GIP_{1-42}$ and $GLP-1_{7-36}$ (or $GLP-1_{7-37}$ or analogues thereof), for example, are broken down to a lesser degree by DPIV or DPIV-like enzymes and hence the reduction in the concentration of those peptide hormones and their analogues is reduced or delayed. The invention is based, therefore, on the finding that a reduction of the DPIV or DPIV-like enzyme activity in the bloodstream results in influencing of the blood sugar level.

The oral administration of the high-affinity, low-molecular-weight enzyme inhibitors of the invention is a more cost-effective alternative, for example, to invasive surgical techniques in the treatment of pathological symptoms. By chemical design of stability, transport and clearance properties their mode of action can be modified and matched to individual characteristics.

The salts of the compounds of the invention may, assuming that they have basic properties, be in the form of inorganic or organic salts.

The compounds of the present invention can be converted into and used as acid addition salts, especially pharmaceutically acceptable acid addition salts. The pharmaceutically acceptable salt generally takes a form in which a basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid. All pharmaceutically acceptable acid addition salt forms of the compounds of the present invention are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

The invention accordingly relates to effectors, especially inhibitors of dipeptidyl peptidase IV (DPIV) and DPIV-like enzyme activity and to their use for lowering the blood sugar level below the glucose concentration characteristic of hyperglycaemia in the serum of a mammal. The invention relates especially to the use of the compounds of the invention for modulating DPIV and DPIV-like enzyme activity in order to prevent or alleviate pathological metabolic abnormalities of mammals, such as, for example, impaired glucose tolerance, glucosuria, hyperlipidaemia, metabolic acidosis, diabetes mellitus, diabetic neuropathy and nephropathy, and sequelae caused by diabetes mellitus in mammals. The invention further relates to the use of the compounds of the invention for modulating DPIV and DPIV-like enzyme activity in order to prevent or alleviate neurodegenerative diseases and high blood pressure. In the case of chronic administration of the compounds of the invention, the invention relates to the improvement of signal action at the cells of the islets of Langerhans and of insulin sensitivity in the peripheral tissue in the postprandial phase.

The invention further relates to the use of the compounds of the invention for the chronic treatment of chronic metabolic diseases in humans; for the chronic treatment of chronically impaired glucose tolerance, chronic glucosuria, chronic hyper-lipidaemia, chronic metabolic acidosis, chronic diabetes mellitus, chronic diabetic neuropathy and nephropathy and of chronic sequelae caused by diabetes mellitus, chronic neurodegenerative diseases and chronic disturbance of signal action at the cells of the islets of Langerhans and chronic insulin sensitivity in the peripheral tissue in the postprandial phase of mammals; for the chronic treatment of chronic metabolism-related hypertension and of chronic cardiovascular sequelae caused by hypertension in mammals; for the chronic treatment of chronic psychosomatic, chronic neuropsychiatric and depressive illnesses, such as chronic anxiety, chronic depression, chronic sleep disorders, chronic fatigue, chronic schizophrenia, chronic epilepsy, chronic nutritional disorders, spasm and chronic pain.

The compounds of the present invention act as prodrugs of DPIV-inhibitors. According to the invention, the compounds can be used as effectors, especially as inhibitors of DPIV and DPIV-like enzymes and it is possible to define the site of their action, the time of onset of their action and the duration of action precisely.

Upon administration, the compounds of the invention are cleaved, for example by suitable enzymes, and the active inhibitors are released. The active inhibitors can be released both by chemical and enzymatic mechanisms. For example, esterases, proteases and peptidases serve to release the active inhibitors from the compounds according to the invention. Such esterases, proteases, etc. are disclosed, for example, in WO 97/45117, U.S. Pat. Nos. 5,433,955, 5,614,379 and 5,624,894. Preferred proteases are aminopeptidases, dipeptidyl aminopeptidases, endoproteases, and endopeptidases. Especially preferred proteases for the release of the active inhibitors from the compounds of the present invention are aminopeptidase N, aminopeptidase P, pyroglutaminyl aminopeptidase, dipeptidyl peptidase IV and dipeptidyl peptidase IV-like enzymes.

The released active inhibitors can interact with the DPIV and DPIV-like enzymes. As a direct result, for example, the above-mentioned insulinotropic peptides are broken down to a lesser degree and the effectiveness of insulin is thereby increased.

The administration of unstable inhibitors of DPIV per se has disadvantages since they are degraded very rapidly in vivo and thus an even-distribution of the inhibitors, especially in the human body, is impossible. In particular, upon oral administration such inhibitors are so unstable that they have virtually no activity at all. Accordingly, stable inhibitors have hitherto been used especially in the treatment of diabetes mellitus.

The present invention uses the concept to stabilize unstable inhibitors by masking them in prodrug form.

The properties of the active inhibitors according to the invention can be designed in such a way that the deactivation time of the DPIV-inhibitors e.g. by intramolecular cyclisation after their release from the prodrugs, is definable.

In particular, the compounds according to the invention have the advantage that the active inhibitors of DPIV and DPIV-like enzymes are released according to individual patients' needs.

When a compound according to the invention interacts with a DPIV molecule or a aminopeptidase N molecule, it is cleaved by these enzymes and the active inhibitor is released. The active inhibitor will inhibit DPIV and/or DPIV-like enzymes so that DPIV itself cannot cleave any further compounds for a defined time. The remaining compounds are not degraded during this defined time and thus, constitute an inhibitor reservoir until the concentration of DPIV molecules or aminopeptidase N molecules rises again or active inhibitor molecules are eliminated or inactivated.

The invention has the further advantage that each organism will release exactly that amount of active inhibitor that is necessary to inhibit that amount of DPIV molecules, which is present in the body of the respective organism.

The present invention accordingly relates to novel compounds of unstable inhibitors of the serine protease dipeptidyl peptidase IV or DPIV-like enzymes, which can be used in the treatment of various disorders, especially of metabolic disorders associated with diabetes mellitus.

Surprisingly such masked inhibitors are additionally considerably more effective than non-masked inhibitors: if identical amounts of non-masked DP IV-inhibitors and of compounds according to the invention are used, the compounds according to the invention produce a marked improvement in glucose tolerance in Diabetic Zucker rats.

The compounds according to the present invention, are transported through the mucosa of the small intenstine without delay, for example simultaneously with nutrient intake.

Moreover, the site of action, at which the active DPIV-inhibitors are released can also be controlled by their structure.

To summarise, it may be stated that, using the compounds of the present invention, it is possible in a completely surprising manner:

1. to achieve increased action of the inhibitors;
2. to release the active inhibitors according to the patient's needs;
3. to release the active inhibitors in a temporally controlled manner;
4. to release the active inhibitors in a site-specific manner; and
5. to provide a reservoir of DPIV-inhibitors.

DETAILED DESCRIPTION AND BEST MODE

As indicated above, the compounds of the present invention, and their corresponding pharmaceutically acceptable acid addition salt forms, are useful in inhibiting DPIV and DPIV-like enzyme activity. The ability of the compounds of the present invention, and their corresponding pharmaceutically acceptable salt forms to inhibit DPIV and DPIV-like enzyme activity may be demonstrated employing the DPIV activity assay for determination of the $K_i$-values and the $IC_{50}$-values in vitro, as described in examples 2 and 3.

The ability of the compounds of the present invention, and their corresponding pharmaceutically acceptable acid addition salt forms to inhibit DPIV in vivo may be demonstrated by oral or intravasal administration to Wistar rats, as described in example 6. The compounds of the present invention inhibit DPIV activity in vivo after both, oral and intravasal administration to Wistar rats.

DPIV is present in a wide variety of mammalian organs and tissues e.g. the intestinal brush-border (Gutschmidt S. et al., "In situ"—measurements of protein contents in the brush border region along rat jejunal villi and their correlations with four enzyme activities. Histochemistry 1981, 72 (3), 467-79), exocrine epithelia, hepatocytes, renal tubuli, endothelia, myofibroblasts (Feller A. C. et al., A monoclonal antibody detecting dipeptidylpeptidase IV in human tissue. Virchows Arch. A. Pathol. Anat. Histopathol. 1986; 409 (2):263-73), nerve cells, lateral membranes of certain surface epithelia, e.g. Fallopian tube, uterus and vesicular gland, in the luminal cytoplasm of e.g., vesicular gland epithelium, and in mucous cells of Brunner's gland (Hartel S. et al., Dipeptidyl peptidase (DPP) IV in rat organs. Comparison of immunohistochemistry and activity histochemistry. Histochemistry 1988; 89 (2): 151-61), reproductive organs, e.g. cauda epididymis and ampulla, seminal vesicles and their secretions (Agrawal & Vanha-Perttula, Dipeptidyl peptidases in bovine reproductive organs and secretions. Int. J. Androl. 1986, 9 (6): 435-52). In human serum, two molecular forms of dipeptidyl peptidase are present (Krepela E. et al., Demonstration of two molecular forms of dipeptidyl peptidase IV in normal human serum. Physiol. Bohemoslov. 1983, 32 (6): 486-96). The serum high molecular weight form of DPIV is expressed on the surface of activated T cells (Duke-Cohan J. S. et al., Serum high molecular weight dipeptidyl peptidase IV (CD26) is similar to a novel antigen DPPT-L released from activated T cells. J. Immunol. 1996, 156 (5): 1714-21).

The compounds of the present invention, and their corresponding pharmaceutically acceptable acid addition salt forms are able to inhibit DPIV in vivo. In one embodiment of the present invention, all molecular forms, homologues and epitopes of DPIV from all mammalian tissues and organs, also of those, which are undiscovered yet, are intended to be embraced by the scope of this invention.

Among the rare group of proline-specific proteases, DPIV was originally believed to be the only membrane-bound enzyme specific for proline as the penultimate residue at the amino-terminus of the polypeptide chain. However, other molecules, even structurally non-homologous with the DPIV but bearing corresponding enzyme activity, have been identified recently. DPIV-like enzymes, which are identified so far, are e.g. fibroblast activation protein α, dipeptidyl peptidase IV β, dipeptidyl aminopeptidase-like protein, N-acetylated α-linked acidic dipeptidase, quiescent cell proline dipeptidase, dipeptidyl peptidase II, attractin and dipeptidyl peptidase IV related protein (DPP 8), and are described in the review article by Sedo & Malik (Sedo & Malik, Dipeptidyl peptidase IV-like molecules: homologous proteins or homologous activities? Biochimica et Biophysica Acta 2001, 36506: 1-10). Further DPIV-like enzymes are disclosed in WO 01/19866, WO 02/34900 and WO02/31134. WO 01/19866 discloses novel human dipeptidyl aminopeptidase 8 (DPP8) with structural and functional similarities to DPIV and fibroblast activation protein (FAP). WO 02/34900 discloses a novel dipeptidyl peptidase 9 (DPP9) with significant homology to the amino acid sequences of DPIV and DPP8. WO 02/31134 discloses three DPIV-like enzymes, DPRP1, DPRP2 and DPRP3.

In another preferred embodiment of the present invention, all molecular forms, homologues and epitopes of proteins comprising DPIV-like enzyme activity, from all mammalian tissues and organs, also of those, which are undiscovered yet, are intended to be embraced by the scope of this invention.

The ability of the compounds of the present invention, and their corresponding pharmaceutically acceptable acid addition salt forms to inhibit DPIV-like enzymes may be demonstrated employing an enzyme activity assay for determination of the $K_i$-values in vitro as described in example 4.

In another embodiment, the compounds of the present invention, and their corresponding pharmaceutically acceptable acid addition salt forms have only low, if no inhibitory activity against non-DPIV and non-DPIV-like proline specific enzymes. See therefore example 5.

In view of their ability to inhibit DPIV and DPIV-like enzyme activity, the compounds of the present invention, and their corresponding pharmaceutically acceptable acid addition salt forms, are useful in treating conditions mediated by said enzyme activities. Based on the findings described in the examples of the present invention and in the literature, it can be shown that the compounds disclosed herein are useful in the treatment of conditions such as immune, autoimmune disorders or central nervous system disorders, selected from the group consisting of strokes, tumors, ischemia, Parkinson's disease, and migraines.

In a more preferred embodiment of this invention, the compounds of the present invention and their corresponding pharmaceutically acceptable acid addition salt forms, improve glucose tolerance by lowering elevated blood glucose levels in response to an oral glucose challenge and, therefore, are useful in treating non-insulin-dependent diabetes mellitus. The ability of the compounds of the present invention, and their corresponding pharmaceutically acceptable acid addition salt forms, to improve glucose tolerance in response to an oral glucose challenge, may be measured in diabetic Zucker rats. The method is described in example 7.

The present invention therefore provides a method of preventing or treating a condition mediated by modulation of the DPIV or DPIV-like enzyme activity in a subject in need thereof which comprises administering any of the compounds of the present invention or pharmaceutical compositions thereof in a quantity and dosing regimen therapeutically effective to treat the condition. Additionally, the present invention includes the use of the compounds of this invention, and their corresponding pharmaceutically acceptable acid addition salt forms, for the preparation of a medicament for the prevention or treatment of a condition mediated by modulation of the DPIV activity in a subject. The compound may be administered to a patient by any conventional route of administration, including, but not limited to, intravenous, oral, subcutaneous, intramuscular, intradermal, parenteral and combinations thereof.

In a further preferred form of implementation, the invention relates to pharmaceutical compositions, that is to say, medicaments, that contain at least one compound of the invention or salts thereof, optionally in combination with one or more pharmaceutically acceptable carriers and/or solvents.

The pharmaceutical compositions may, for example, be in the form of parenteral or enteral formulations and contain appropriate carriers, or they may be in the form of oral formulations that may contain appropriate carriers suitable for oral administration. Preferably, they are in the form of oral formulations.

The pharmaceutical compositions may additionally contain one or more hypoglycaemically active ingredients which may be active ingredients that are known per se.

The effectors of DP IV and DPIV-like enzymes administered according to the invention may be employed in pharmaceutically administrable formulations or formulation complexes as inhibitors or in combination with inhibitors, substrates, pseudosubstrates, inhibitors of DP IV expression, binding proteins or antibodies of those enzyme proteins that reduce the DP IV and DPIV-like protein concentration in mammals. The compounds of the invention make it possible to adjust treatment individually to patients and diseases, it being possible, in particular, to avoid individual intolerances, allergies and side-effects.

The compounds also exhibit differing degrees of activity as a function of time. The doctor providing treatment is thereby given the opportunity to respond differently to the individual situation of patients: he is able to adjust precisely, on the one hand, the speed of the onset of action and, on the other hand, the duration of action and especially the intensity of action.

The method according to the Invention represents especially a new approach to the reduction of raised blood glucose concentration in the serum of mammals. It is simple, susceptible of commercial application and suitable for use in the treatment of especially diseases that are based on above-average blood glucose values, on neurodegenerative diseases or on high blood pressure, in mammals and especially in human medicine.

The compounds are administered, for example, in the form of pharmaceutical preparations that contain the active ingredient in combination with customary additives like diluents, excipients and/or carriers known from the prior art. For example, they are administered parenterally (for example i.v. in physiological saline solution) or enterally (for example orally, formulated with customary carriers, such as, for example, glucose).

Depending upon their endogenous stability and their bioavailability, one or more doses of the compounds can be given per day in order to achieve the desired normalisation of the blood glucose values. For example, such a dosage range in humans may be in the range of from 0.01 mg to 250.0 mg per day, preferably in the range of from 0.01 to 100 mg of compound per kilogram of body weight.

It has been found that by administering effectors of dipeptidyl peptidase IV and DPIV-like enzyme activities in the blood of a mammal, owing to the associated temporary reduction in activity, the endogenous (or additionally exogenously administered) insulinotropic peptides Gastric Inhibitory Polypeptide 1-42 ($GIP_{1-42}$) and Glucagon-Like Peptide Amide-1 7-36 ($GLP-1_{7-36}$) (or other $GLP-1_{7-37}$ or analogues thereof) are, as a consequence, broken down to a lesser extent by DP IV and DP IV-like enzymes and hence the reduction in the concentration of those peptide hormones and their analogues is reduced or delayed. The increased stability of the (endogenous or exogenously supplied) incretins or their analogues, which is achieved owing to the action of DP IV effectors and which results in their being available in greater quantities for insulinotropic stimulation of the incretin receptors of the Langerhans cells in the pancreas, alters inter alia the effectiveness of the body's own insulin, which brings with it a stimulation of the carbohydrate metabolism of the subject treated.

As a result, the blood sugar level falls below the glucose concentration characteristic of hyperglycaemia in the serum of the subject treated. Accordingly, it is possible to prevent or alleviate metabolic abnormalities, such as impaired glucose tolerance, glucosuria, hyperlipidaemia, metabolic acidosis, diabetes mellitus, diabetic neuropathy and nephropathy and sequelae caused by diabetes mellitus in mammals, metabolism-related hypertension and cardiovascular sequelae caused by hypertension in mammals, skin diseases and diseases of the mucosae, autoimmune diseases, high blood pressure and inflammatory conditions, and psychosomatic, neuropsychiatric and depressive illnesses, such as anxiety, depression, sleep disorders, chronic fatigue, schizophrenia, epilepsy, nutritional disorders, spasm and chronic pain.

To enhance the blood-sugar-reducing action of various antidiabetics, combinations of various orally active antidiabetics are often used. Since the antihyperglycaemic action of the compounds of the invention operates independently of other known orally administrable antidiabetics, the active ingredients of the invention are analogously suitable for use in combination therapies, in an appropriate galenical form, for achieving the desired normoglycaemic effect.

The compounds used according to the invention can accordingly be converted in a manner known per se into conventional formulations, such as, for example, tablets, capsules, dragées, pills, suppositories, granules, aerosols, syrups, liquid, solid and cream-like emulsions and suspensions and solutions, using inert, non-toxic, pharmaceutically suitable carriers and additives or solvents. In each of those formulations, the therapeutically effective compounds are preferably present in a concentration of approximately from 0.1 to 80% by weight, preferably from 1 to 50% by weight, of the total mixture, that is to say, in amounts sufficient for the mentioned dosage latitude to be obtained.

The good absorption of the compounds used according to the invention by the mucosae of the gastrointestinal tract makes it possible for many galenical preparations to be used:

The substances can be used as medicaments in the form of dragées, capsules, bitable capsules, tablets, drops, syrups or also as suppositories or as nasal sprays.

The formulations are prepared, for example, by extending the active ingredient with solvents and/or carriers, optionally with the use of emulsifiers and/or dispersants, it being possible, for example, in the case where water is used as diluent, for organic solvents to be optionally used as auxiliary solvents.

There may be mentioned as examples of excipients: water, non-toxic organic solvents, such as paraffins (for example natural oil fractions), vegetable oils (for example rapeseed oil, groundnut oil, sesame oil), alcohols (for example ethyl alcohol, glycerol), glycols (for example propylene glycol, polyethylene glycol), solid carriers, such as, for example, natural powdered minerals (for example highly disperse silica, silicates), sugars (for example raw sugar, lactose and dextrose), emulsifiers, such as non-ionic and anionic emulsifiers (for example polyoxyethylene fatty acid esters, polyoxyethylene fatty alcohol ethers, alkylsulphonates and arylsulphonates), dispersants (for example lignin, sulphite liquors, methylcellulose, starch and polyvinylpyrrolidone) and lubricants (for example magnesium stearate, talcum, stearic acid and sodium lauryl sulphate) and optionally flavourings.

Administration is carried out in the usual manner, preferably enterally or parenterally, especially orally. In the case of enteral administration, tablets may contain in addition to the mentioned carriers further additives such as sodium citrate, calcium carbonate and calcium phosphate, together with various additives, such as starch, preferably potato starch, gelatin and the like. Furthermore, lubricants, such as magnesium stearate, sodium lauryl sulphate and talcum, can be used concomitantly for tabletting. In the case of aqueous suspensions and/or elixirs intended for oral administration, various taste correctives or colourings can be added to the active ingredients in addition to the above-mentioned excipients.

In the case of parenteral administration, solutions of the active ingredients using suitable liquid carriers can be employed. In general, it has been found advantageous to administer, in the case of intravenous administration, amounts of approximately from 0.01 to 2.0 mg/kg, preferably approximately from 0.01 to 1.0 mg/kg, of body weight per day to obtain effective results and, in the case of enteral administration, the dosage is approximately from 0.01 to 2 mg/kg, preferably approximately from 0.01 to 1 mg/kg, of body weight per day.

It may nevertheless be necessary in some cases to deviate from the stated amounts, depending upon the body weight of the experimental animal or the patient or upon the type of administration route, but also on the basis of the species of animal and its individual response to the medicament or the interval at which administration is carried out. Accordingly, it may be sufficient in some cases to use less than the above-mentioned minimum amount, while, in other cases, the mentioned upper limit will have to be exceeded. In cases where relatively large amounts are being administered, it may be advisable to divide those amounts into several single doses over the day. For administration in human medicine, the same dosage latitude is provided. The above remarks apply analogously in that case.

EXAMPLES OF PHARMACEUTICAL FORMULATIONS

1. Capsules containing 100 mg of a compound of the invention per capsule:

For approximately 10,000 capsules a solution of the following composition is prepared:

| compound of the invention | 1.0 kg |
| glycerol | 0.5 kg |
| polyethylene glycol | 3.0 kg |
| water | 0.5 kg |
| | 5.0 kg |

The solution is introduced into soft gelatin capsules in a manner known per se. The capsules are suitable for chewing or swallowing.

2. Tablets or coated tables or dragées containing 100 mg of a compound of the invention:

The following amounts refer to the preparation of 100,000 tablets: compounds of the invention,

| finely ground | 10.0 kg |
| glucose | 4.35 kg |
| lactose | 4.35 kg |
| starch | 4.50 kg |
| cellulose, finely ground | 4.50 kg |

The above constituents are mixed and then provided with a solution prepared from

| polyvinylpyrrolidone | | 2.0 kg |
| polysorbate | | 0.1 kg |
| and water | approx. | 5.0 kg | and granulated in a manner known per se by grating the moist mass and, after the addition of 0.2 kg of magnesium stearate, drying it. The finished tablet mixture of 30.0 kg is processed to form convex tablets weighing 300 mg. The tablets can be coated or sugar-coated in a manner known per se.

EXAMPLES OF THE INVENTION

Example 1

Synthesis of Peptidylketones

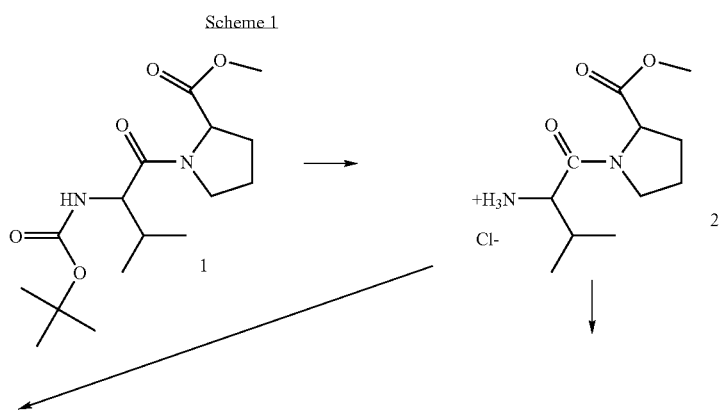

Scheme 1

-continued

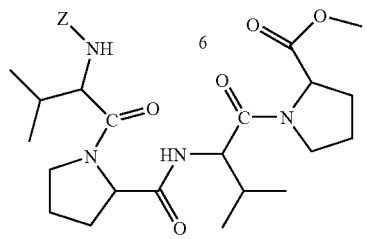

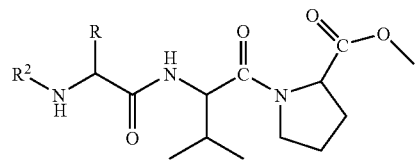

5: R = CH₃, R² = Z
7: R = H, R² = Z
8: R = CH₃, R² = Boc

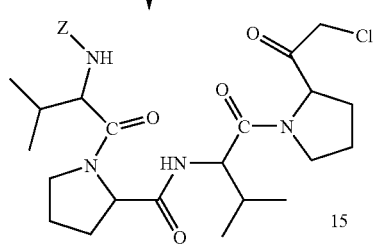

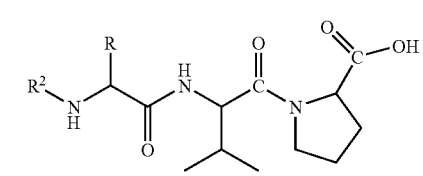

9: R = CH₃, R² = Z
11: R = H, R² = Z
12: R = CH₃, R² = Boc

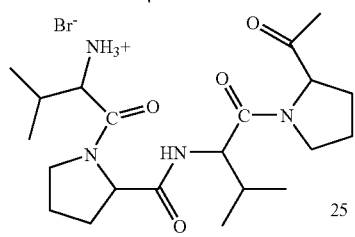

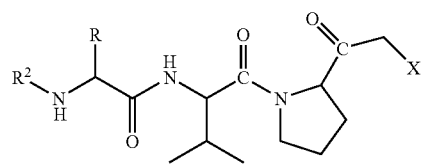

13: R = CH₃, R² = Z, X = Br
14: R = CH₃, R² = Z, X = Cl
16: R = H, R² = Z, X = Br
17: R = CH₃, R² = Boc, X = Br

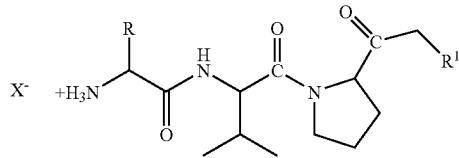

| | | | |
|---|---|---|---|
| 24: R = CH₃, | R¹ = H, | X = Br | |
| 26: R = CH₃, | R¹ = OC(O)Ac, | X = Br | |
| 27: R = CH₃, | R¹ = OC(O)Ph, | X = Br | |
| 28: R = CH₃, | R¹ = SCH₂DCP, | X = TFA | |
| 29: R = H, | R¹ = OC(O)Ph, | X = Br | |

| | | | |
|---|---|---|---|
| 18: R = H, | R¹ = H, | R² = Z |
| 20: R = CH₃, | R¹ = OC(O)Ac, | R² = Z |
| 21: R = CH₃, | R¹ = OC(O)Ph, | R² = Z |
| 22: R = CH₃, | R¹ = SCH₂DCP, | R² = Boc |
| 23: R = H, | R¹ = OC(O)Ph, | R² = Z |

H-Val-Pro-OMe*HCl 2

Boc-Val-OH (3.00 g, 13.8 mmol) was dissolved in 10 ml of dry THF and cooled down to −15° C. To the mixture CAIBE (1.80 ml, 13.8 mmol) and NMM (1.52 ml, 13.8 mmol) were added and the solution was stirred until the formation of the mixed anhydride was complete. Then the mixture was brought to −10° C. and NMM (1.52 ml, 13.8 mmol) was added followed by H-Pro-OMe*HCl (2.29 g, 13.8 mmol). The mixture was allowed to reach r.t. and left overnight.

After removing the solvent and the usual workup the resulting ester 1 was taken without further characterisation.

1 was dissolved in HCl/HOAc (5 ml, 6N) and left at 0° C. until the removal of the Boc-group was complete. Then the solvent was removed and the resulting oil was treated with diethylether to give a white solid 2.

Yield: 2.5 g, 80%

Z-Val-Pro-OMe 3

Z-Val-OH (3.5 g, 13.9 mmol) and H-Pro-OMe*HCl (2.14 g, 13.9 mmol) were treated in the same manner as above for 1, to give 3 as a white solid.

Yield: 3.76 g, 80%

Z-Val-Pro-OH 4

3 (3.76 g, 10.4 mmol) was dissolved in 30 ml of water/acteone (1/5 v/v) and 11.4 ml NaOH (1N) was added. After completion of the reaction the organic solvent was removed by evaporation and the resulting solution was diluted by 15 ml NaHCO3 solution (saturated). Then the mixture was extracted three times by 10 ml of acetic acid ethyl ester. After that the solution was brought to pH2 by adding HCl (15% in water). The resulting mixture was extracted three times by 30 ml of acetic acid ethyl ester. The organic layer was separated and washed three times with brine, dried (Na2SO4) and evaporated.

Yield: 3.25 g, 90%

Z-Ala-Val-Pro-OMe 5
Z-Ala-OH (3.5 g, 15.7 mmol) and 2 (4.18 g, 15.7 mmol) were treated in the same manner as above for 1, to give 5 as a white solid.
Yield: 4.2 g, 64%

Z-Val-Pro-Val-Pro-OMe 6
4 (3.76 g, 10.08 mmol) and 2 (2.19 g 10.08 mmol) were treated in the same manner as above for 1, to give 6 as a white solid.
Yield: 4.21 g, 70%

Z-Gly-Val-Pro-OMe 7
Z-Gly-OH (1.55 g 7.45 mmol) and 2 (1.51 g, 7.45 mmol) were treated in the same manner as above for 1, to give 7 as an oil.
Yield: 2.99 g, 96%

Boc-Ala-Val-Pro-OMe 8
Boc-Ala (1.29 g, 6,.80 mmol) and 2 (1.80 g, 6,.80 mmol) were treated in the same manner as above for 1, to give 8 as a white solid.
Yield: 2.24 g, 83.1%

Z-Ala-Val-Pro-OH 9
5 (4.15 g, 9.6 mmol) was treated in the same manner as above for 4, to give 9 as a white solid.
Yield: 3.5 g, 87%

Z-Val-Pro-Val-Pro-OH 10
6 (4.21 g, 7.5 mmol) was treated in the same manner as above for 4, to give 10 as a white solid.
Yield: 3.89 g, 95%

Z-Gly-Val-Pro-OH 11
7 (2.99 g, 7.15 mmol) was treated in the same manner as above for 4, to give 11 as a white solid.
Yield: 1.88 g, 65%

Boc-Ala-Val-Pro-OH 12
8 (1 g, 2.50 mmol) was treated in the same manner as above for 4, to give 12 as a white solid.
Yield: 0.88 g, 89.1%

Z-Ala-Val-Pro-$CH_2$—Br 13
9 (2.00 g, 4.76 mmol) was dissolved in 15 ml of dry THF and converted into a mixed anhydride (see compound 1) using CAIBE (0.623 ml, 4.76 mmol) and NMM (0.525 ml, 4.76 mmol). The precipitate formed was filtered off and cooled down to −15° C. Then diazomethane (23.8 mmol in 30 ml ether) was dropped into the solution under an argon atmosphere. After leaving the mixture for 1 h at 0° C. 1.27 ml of HBr (33% in AcOH) was added and the solution was stirred for 30 min at r.t.. After that 70 ml of ether was added and the mixture was washed 20 ml of water. The organic layer was separated and dried (Na2SO4) and evaporated.
Yield (crude): 1.8 g, 80%

Z-Ala-Val-Pro-$CH_2$—Cl 14
9 (1.02 g, 2.43 mmol) was treated as described for 13 using CAIBE (0.315 ml, 2.43 mmol), NMM (0.267 ml, 2.43 mmol), diazomethane (12.2 mmol in 16 ml ether) and 5 ml of HCl in dioxane (7.6M).
Yield (crude): 1 g, 91%

Z-Val-Pro-Val-Pro-$CH_2$—Cl 15
10 (1.1 g, 2.01 mmol) was treated as described for 13 using CAIBE (0.263 ml, 2.01 mmol), NMM (0.223 ml, 2.02 mmol), diazomethane (10 mmol in 13.3 ml ether) and 5 ml of HCl in dioxane (7.6M).
Yield (crude): 1.1 g, 95%

Z-Gly-Val-Pro-$CH_2$—Br 16
11 (2.04 g, 5.05 mmol) was treated as described for 13 using CAIBE (0.656 ml, 5.05 mmol), NMM (0.556 ml, 5.05 mmol), diazomethane (10 mmol in 13.3 ml ether) and 5 ml of HCl in dioxane (7.6M).
Yield (crude): 2.10 g, 90.4%

Boc-Ala-Val-Pro-$CH_2$Br 17
12 (0.88 g, 2.28 mmol) was treated as described for 13, using CAIBE (2.28 mmol, 0.37 ml), NMM (2.28 mmol, 0.31 ml), diazomethane (14.3 mmol in 15 ml ether) HBr/glacial acetic acid (33%): 4.24 mmol, 1.04 ml.
Yield: 0.88 g, 83.4%

Z-Protected Methylketones

Z-Ala-Val-Pro-$CH_3$ 18
14 (1 g, 2.21 mmol) was dissolved in 5.30 ml of warm acidic acid and 1.33 g of zinc-powder was added portion wise to the stirred solution. After 24 h the remaining solid was filtered off and the filtrate was evaporated. The remaining oil was taken up in ethylacetate and washed twice with $NaHCO_3$ and brine. The organic layer was then dried and evaporated and purified by column chromatography using a heptane/chloroform/methanol-gradient.
Yield: 0.230 g, 24.8%

Z-Val-Pro-Val-Pro-$CH_3$ 19
15 (1.1 g, 1.91 mmol) was treated as described for 18 using acidic acid (5.3 ml) and zinc (1.31 g).
Yield: 0.190 g, 16%

N-Protected Acyloxymethylene Ketones
The acid (2 eq) was dissolved in DMF and an equimolar amount of KF was added. The suspension was allowed to stir at r.t. for 1 h. Then the brommethylene (1 eq) component was added and the solution was allowed to stir overnight. After that the solvent was removed under vacuum and the resulting oil was dissolved in chloroform and washed with brine. Then the organic layer was separated dried ($Na_2SO_4$) and the solvent was removed. The product was purified by column chromatography using silica gel and heptane/chloroform.

Z-Ala-Val-Pro-$CH_2$O—C(O)—$CH_3$ 20
Acetic acid (230 µl, 4.02 mmol), KF (0.234 g, 4.02 mmol), 13 (1.00 g, 2.01 mmol).
Yield: 0.351 g, 36%

Z-Ala-Val-Pro-$CH_2$O—C(O)-Ph 21
Benzoic acid (0.275 g, 2.25 mmol), KF (0.131 mg, 2.25 mmol), 13 (0.56 g, 1.13 mmol).
Yield: 0.34 g, 56%

Boc-Ala-Val-Pro-$CH_2$—S—$CH_2$-Dichlorphenyl 22
Dichlorobenzylmercaptane (0.30 ml, 2.09 mmol), KF (0.250 g, 4.19 mmol), 17 (0.88 g, 1.9 mmol).
Yield: 0.56 g, 51%

Z-Gly-Val-Pro-$CH_2$O—C(O)-Ph 23
Benzoic acid (1.19 g, 9.78 mmol), KF (0.568 g, 9.78 mmol), 16 (2.35 g, 4.89 mmol).
Yield: 0.89 g, 34.8%

Deprotection

Method A:
The Z-protected compound was dissolved in HBr/AcOH and stirred. When the reaction was complete ether was added, the white precipitate formed was filtered off and dried.

Method B:

The Boc-protected compound was dissolved in TFA and stirred. When the reaction was complete ether was added, the white precipitate formed was filtered off and dried.

H-Ala-Val-Pro-CH₃*HBr 24

Method A
  18 (0.230 g, 0.54 mmol)
  Yield: 0.124 g, 80%

H-Val-Pro-Val-Pro-CH₃*HBr 25

Method A
  19 (0.190 g, 0.20 mmol)
  Yield: 0.114 g, 82.3%

H-Ala-Val-Pro-CH₂O—C(O)CH₃*HBr 26

Method A
  20 (0.351 g, 0.73 mmol)
  Yield: 0.252 g, 98%

H-Ala-Val-Pro-CH₂O—C(O)Ph*HBr 27

Method A
  21 (0.34 g, 0.63 mmol)
  Yield: 0.251 g, 99%

H-Ala-Val-Pro-CH₂—S—CH₂-Dichlorphenyl*TFA 28

Method B
  22 (0.56 g, 0.97 mmol)
  Yield: 0.027 g, 5%

H-Gly-Val-Pro-CH₂O—C(O)Ph*HBr 29

Method A
  23 (0.156 g, 0.26 mmol)
  Yield: 0.115 g, 99%

Scheme 2

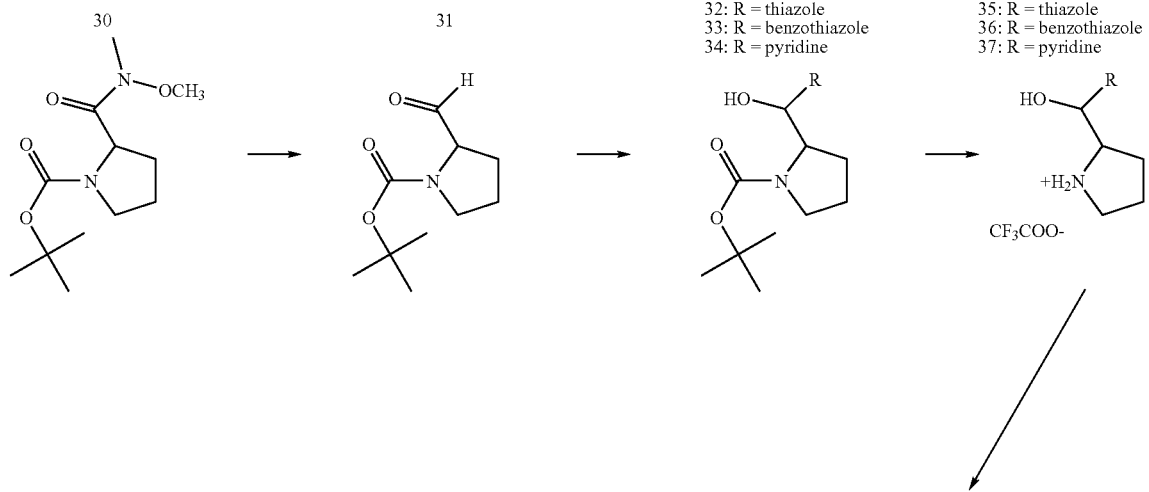

38: R = thiazole,      R¹ = Me
39: R = benzothiazole  R¹ = Me
40: R = benzothiazole  R¹ = H
41: R = pyridine       R¹ = Me

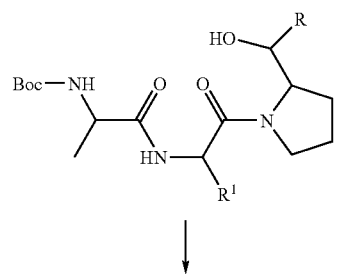

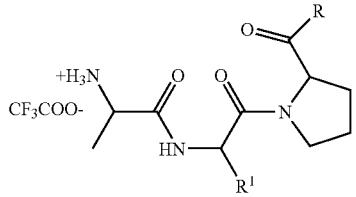 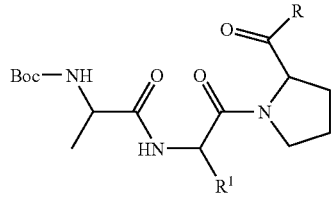

| 46: R = thiazole, | R¹ = Me |
| 47: R = benzothiazole | R¹ = Me |
| 48: R = benzothiazole | R¹ = H |
| 49: R = pyridine | R¹ = Me |

| 42: R = thiazole, | R¹ = Me |
| 43: R = benzothiazole | R¹ = Me |
| 44: R = benzothiazole | R¹ = H |
| 45: R = pyridine | R¹ = Me |

Boc-Pro-N(Me)OMe 30

Boc-Proline (2.00 g, 9.29 mmol) and N,O-Dimethylhydroxylaminehydrochloride (0.91 g, 9.29 mmol) were treated as described for 1 using NMM (2 ml, 18.4 mmol) and CAIBE (1.47 ml, 9.29 mmol).

Yield: 2.1 g, 87.5%

Boc-Prolinal 31

10 mmol of 30 was dissolved in 20 ml of absolute ether at 0° C. 12.5 mmol lithiumalanate was added. After 7 min of stirring 10 ml of a saturated KHSO₄ solution was added drop wise. Then the mixture was diluted by adding 50 ml of ether and the organic layer was separated. This was washed by 1N HCl, water, saturated NaHCO₃ solution, brine and dried. 30 (1.43 g, 5.54 mmol), LiAlH₄ (0.26 g, 6.92 mmol)

Yield: 0.78 g, 70.8%

2-Heterocyclo-hydroxymethyl-N-Boc-(2S)-pyrrolidines 1.1 eq of the heterocycle was dissolved in 5 ml of dry THF under argon atmosphere and brought to −65° C. 1.1 eq of n-Butyllithium (1.6 M in hexane) was added and the solution was stirred at −65° C. for 1 h. 1 eq of 31, dissolved in 2 ml dry THF, was dropped into the stirred solution and the mixture was stirred at −65° C. for 2 h. After that 2 ml of water was added and the solution was extracted three times using methylene chloride. The organic layer was separated, dried and evaporated.

2-[([1,3]-Thiazol-2-yl)hydroxymethyl]-1-N-(tert-butoxycarbonyl)-(2S)-pyrrolidine 32

31 (1.0 g, 5.02 mmol), thiazole (0.39 ml, 5.52 mmol), n-BuLi (1.6 M) (3.45 ml 5.52 mmol).

Yield: 1.02 g, 71.0%

2-[(Benzothiazol-2-yl)hydroxymethyl]-1-N-(tert-butoxycarbonyl)-(2S)-pyrrolidine 33

31 (1.0 g, 5.02 mmol), benzothiazole (0.6 ml, 5.52 mmol), n-BuLi (1.6M) (3.45 ml 5.52 mmol).

Yield: 1.73 g, 78.0%

2-[(Pyridin-2-yl)hydroxymethyl]-1-N-(tert-butoxycarbonyl)-(2S)-pyrrolidine 34

31 (1.3 g, 6.54 mmol), 2-bromopyridine (0.70 ml, 7.19 mmol), n-BuLi (1.6M) (4.5 ml, 7.19 mmol)

Yield: 1.68 g, 92.2%.

2-Heterocyclo-hydroxymethyl-(2S)-pyrrolidines 32, 33 and 34 where treated as described for 2.

2-[([1,3]-Thiazol-2-yl)hydroxymethyl]-(2S)-pyrrolidine hydrochloride 35

32 (0.46 g, 1.62 mmol)

Yield: 0.34 g, 94.9%

2-[(Benzothiazol-2-yl)hydroxymethyl]-(2S)-pyrrolidine hydrochloride 36

33 (0.6 g, 1.79 mmol)

Yield: 0.436 g, 90%

2-[(Pyridin-2-yl)hydroxymethyl]-(2S)-pyrrolidine hydrochloride 37

34 (0.95 g, 3.41 mmol)

Yield: 0.71 g, 96.8%

N protected 2-Heterocyclo-hydroxymethyl-N-Peptidyl-(2S)-pyrrolidines 1 eq of a Boc-Ala-Val-OH or Boc-Ala-Gly-OH and 1 eq of N-hydroxysuccinimide were dissolved in dioxane. At 0° C. 1 eq of dicyclohexylcarbodiimide was added and the solution was stirred for 2 h. After stirring overnight at r.t. the precipitate was removed. The organic phase was washed with a saturated solution of NaHCO3 and brine. After drying the solvent was removed.

The active ester was dissolved with 1 eq of 35 in dry THF and brought to 0° C. 1 eq of triethylamine was added and stirred for 2 h at 0° C. The solvent was removed and the resulting oil was dissolved in ethyl acetate. After washing with 1N HCl, water, a saturated solution of NaHCO₃ and brine the solvent was removed after drying. The mixture was purified by column chromatography using a heptane/chloroform gradient.

2-[([1,3]-Thiazol-2-yl)hydroxymethyl]-1-{N-[N-(tertbutyloxycarbonyl) (L)-Alanyl]-(L)-Valinyl}-(2S)-pyrrolidine 38

35 (0.44 g, 1.54 mmol), N-hydroxysuccinimide (0.17 g, 1.54 mmol), DCC (0.32 g, 1.54 mmol), Boc-Ala-Val-OH (0.34 g, 1.54 mmol), TEA (0.22 ml, 1.54 mmol)

Yield: 0.3 g, 42.9%.

1 eq of Boc-Ala-Val-OH or Boc-Ala-Gly-OH and 0.9 eq of 36 or 37, 1.1 eq of HOBt, and 1.1 eq of WSCD were dissolved in dry ACN. After addition of 0.9 eq of TEA the mixture was stirred overnight. The solvent was removed and the remaining oil was dissolved in ethyl acetate. The solution was washed with brine and dried.

2-[(Benzothiazol-2-yl)hydroxymethyl]-1-{N-[N-(tertbutyloxycarbonyl)-(L)-Alanyl]-(L)-Valinyl}-(2S)-pyrrolidine 39

36 (0.43 g, 1.23 mmol), HOBt (0.183 g, 1.35 mmol), WSCD (0.259 g, 1.35 mmol), Boc-Ala-Val-OH (0.35 g, 1.23 mmol), TEA (0.172 ml, 1.54 mmol)
Yield: 0.3 g, 42.9%

2-[(Benzothiazol-2-yl)hydroxymethyl]-1-{N-[N-(tertbutyloxycarbonyl)(L)-Alanyl]-glycyl}-(2S)-pyrrolidine 40

36 (0.43 g, 1.23 mmol), HOBt (0.183 g, 1.35 mmol), WSCD (0.259 g, 1.35 mmol), Boc-Ala-Val-OH (0.303 g, 1.23 mmol), TEA (0.172 ml, 1.54 mmol)
Yield: 0.41 g, 72%

2-[(Pyridin-2-yl)hydroxymethyl]-1-{N-[N-(tertbutyloxycarbonyl)(L)-Alanyl]-(L)-Valinyl}-(2S)-pyrrolidine 41

37 (0.15 g, 0.52 mmol) Boc-AlaVal-OH (0.1 g, 0.47 mmol); HOBT (0.08 g, 0.57 mmol), WSCD (0.11 g, 0.57 mmol), TEA (0.07 ml, 0.47 mmol)
Yield: 0.22 g, 94.9%

N Protected 2-Heterocyclo-carbonyl-N-Peptidyl-(2S)-pyrrolidines 1.8 eq of oxaylchloride was dissolved in 5 ml of dry dichloromethane and brought to –78° C. under argon atmosphere. A solution of 2.5 eq of DMSO in 2 ml dichloromethane was added and kept for 20 min at –78° C. 1 eq of 38, 39, 40 or 41 was dissolved in 5 ml dichloromethane and added drop wise. The mixture was stirred for 20 min at –78° C. After that 4 eq TEA was added and the mixture was brought to r.t.. 30 ml of a mixture of hexane/ethyl acetate (2/1, v/v) and 10 ml of a 2% HCl (m/V) were added. The organic layer was separated dried and the solvent was removed. The mixture was purified by column chromatography using a heptane/chloroform gradient.

2-[([1,3]-Thiazol-2-yl)carbonyl]-1-{N-[N-(tertbutyloxycarbonyl)(L)-Alanyl]-(L)-Valinyl}-(2S)-pyrrolidine 42

38 (0.15 g, 0.33 mmol), oxalylchloride (0.05 ml, 0.59 mmol), DMSO (0.06 ml, 0.82 mmol), TEA (0.12 ml, 1.32 mmol)
Yield: 0.13 g, 89%

2-[(Benzothiazol-2-yl)carbonyl]-1-{N-[N-(tertbutyloxycarbonyl)-(L)-Alanyl]-(L)-Valinyl}-(2S)-pyrrolidine 43

39 (0.72 g, 0.14 mmol), oxalylchloride (0.221 ml, 2.57 mmol), DMSO (2.53 ml, 3.57 mmol), TEA (0.80 ml, 5.71 mmol)
Yield: 0.049 g, 70%

2-[(Benzothiazol-2-yl)carbonyl]-1-{N-[N -(tertbutyloxycarbonyl)-(L)-Alanyl]-glycyl}-(2S)-pyrrolidine 44

40 (0.62 g, 0.134 mmol), oxalylchloride (0.207 ml, 2.41 mmol), DMSO (2.37 ml, 3.35 mmol), TEA (0.75 ml, 5.35 mmol)
Yield: 0.38 g, 62%

2-[(Pyridin-2-yl)carbonyl]-1-{N-[N-(tertbutyloxycarbonyl)(L)-Alanyl]-(L)-Valinyl}-(2S)-pyrrolidine 45

41 (0.29 g, 0.64 mmol), oxalylchloride (0.10 ml, 1.15 mmol), DMSO (0.11 ml, 1.59 mmol), TEA (0.36 ml, 2.55 mmol)
Yield: 0.14 g, 49.2%

2-Heterocyclo-carbonyl-N-Peptidyl-(2S)-pyrrolidines 42, 43, 44, 45 were treated as described under deprotection method B.

2-[([1,3]-Thiazol-2-yl)carbonyl]-1-N-[{(L)-Alanyl}-(L)-Valinyl]-(2S)-pyrrolidine trifluoroacetate 46

42 (0.13 g, 0.29 mmol)
Yield: 0.04 g, 30.1%

2-[(Benzothiazol-2-yl)carbonyl]-1-N-[{(L)-Alanyl}-(L)-Valinyl]-(2S)-pyrrolidine trifluoroacetate 47

43 (0.49 g, 0.97 mmol)
Yield: 0.24 g, 60.3%

2-[(Benzothiazolethiazol-2-yl)carbonyl]-1-N-[N-{(L)-Alanyl}-Glycyl]-(2S)-pyrrolidine trifluoracetate 48

44 (0.38 g, 0.82 mmol)
Yield: 0.187 g, 60.1%

2-[(Pyridin-2-yl)carbonyl]-1-N-[{(L)-Alanyl}-(L)-Valinyl]-(2S)-pyrrolidine trifluoroacetate 49

45 (0.14 g, 0.31 mmol)
Yield: 0.054 g, 37.7%

From the compounds of the present invention biological efficacy data were investigated. The results are described and discussed in the further examples. In particular, these compounds are:

| Cpd. no. | Short name | Full name |
|---|---|---|
| 24 | H-Ala-Val-Pro-Me*HBr | 2-Methylcarbonyl-1-N-[(L)-Alanyl-(L)-Valinyl]-(2S)-pyrrolidine hydrobromide |
| 25 | H-Val-Pro-Val-Pro-Me*HBr (SEQ ID NO:1) | 2-Methylcarbonyl-1-N-[(L)-Valinyl-(L)-Prolyl-(L)-Valinyl]-(2S)-pyrrolidine hydrobromide |
| 26 | H-Ala-Val-Pro-$CH_2O$—CO—$CH_3$*HBr | 2-[(Acetyloxy-methyl)carbonyl]-1-N-[(L)-Alanyl-(L)-Valinyl]-(2S)-pyrrolidine hydrobromide |
| 27 | H-Ala-Val-Pro-CO—$CH_2O$—CO—Ph*HBr | 2-[(Benzoyloxy-methyl)carbonyl]-1-N-[{(L)-Alanyl}-(L)-Valinyl]-(2S)-pyrrolidine hydrobromide |
| 28 | H-Ala-Val-Pro-CO—$CH_2$—S—$CH_2$-Dichlorphenyl*TFA | 2-{[(2,6-Dichlorobenzyl)thiomethyl]carbonyl}-1-N-[{(L)-Alanyl}-(L)-Valinyl]-(2S)-pyrrolidine |
| 29 | H-Gly-Val-Pro-CO—$CH_2O$—CO—Ph*HBr | 2-[(Benzoyloxy-methyl)carbonyl]-1-N-[Glycyl-(L)-Valinyl]-(2S)-pyrrolidine hydrobromide |
| 46 | H-Ala Val-Pro-CO-Thiazol*TFA | 2-[([1,3]-Thiazol-2-yl)carbonyl]-1-N-[{(L)-Alanyl}-(L)-Valinyl]-(2S)-pyrrolidine trifluoroacetate |
| 47 | H-Ala-Val-Pro-CO-Benzothiazole*TFA | 2-[(Benzothiazol-2-yl)carbonyl]-1-N-[{(L)-Alanyl}-(L)-Valinyl]-(2S)-pyrrolidine trifluoroacetate |
| 48 | H-Ala-Gly-Pro-CO-Benzothiazol*TFA | 2-[(Benzothiazol-2-yl)carbonyl]-1-N-[{(L)-Alanyl}-Glycyl]-(2S)-pyrrolidine trifluoroacetate |
| 49 | H-Ala-Val-Pro-CO-(2-Pyridine)*TFA | 2-[(Pyridin-2-yl)carbonyl]-1-N-[{(L)-Alanyl}-(L)- Valinyl]-(2S)-pyrrolidine trifluoroacetate |

Example 2

$K_i$-Determination

For $K_i$ determination dipeptidyl peptidase IV from porcine kidney with a specific activity against glycylprolyl-4-nitroaniline of 37.5 U/mg and an enzyme concentration of 1.41 mg/ml in the stock solution was used.

Assay Mixture:

500 µl test compound in a concentration range of $1*10^{-5}$ M-$1*10^{-11}$M were admixed with and 500 µl HEPES buffer (40 mM, pH7.6; ion strength=0.125) and 20 µl of diluted DPIV. Release of the inhibitor from the prodrug as well the monitoring reaction (DPIV-catalyzed hydrolysis of Gly-Pro-pNA) were started by addition of a mixture of 10 µl of APN stock solution (4.9 mg/ml, Sigma, Taufkirchen, Germany) with 250 µl of the substrate (Gly-Pro-pNA, 0.05-4 mM). Development of yellow color due to 4-nitroaniline release were monitored at λ=405 nm for up to 180 min using UV1 Spectrometer (ThermoSpectronic).

The $K_i$-values were calculated by fitting the first derivative of the time-progress curves using Graphit (v.4.0.13, Erithacus Software, Ltd, UK) and an equation for an unstable competitive inhibitor.

$$v = \frac{V_{max}*S_0}{S_0 + K_m\left(1 + \frac{I*e^{-kt}}{K_i}\right)}$$

The half-life ($t_{1/2}$) was calculated by plotting the enzyme activity versus reaction time.

2.1 Results-$K_i$ Values of DPIV inhibition

| Compound | Ki [M] | $T_{1/2}$ [min] |
|---|---|---|
| H-Ala-Val-Pro-Me*HBr | $4.76*10^{-8}$ | 12.4 |
| H-Val-Pro-Val-Pro-Me*HBr (SEQ ID NO:1) | n.d. | n.d. |
| H-Ala-Val-Pro-$CH_2O$—CO—$CH_3$*HBr | $1.05*10^{-9}$ | 10.8 |
| H-Ala-Val-Pro-CO—$CH_2O$—CO—Ph*HBr | $5.36*10^{-10}$ | 15.1 |
| H-Gly-Val-Pro-CO—$CH_2O$—CO—Ph*HBr | no inhibition | n.d. |
| H-Ala-Val-Pro-CO-Benzothiazole*TFA | $3.73*10^{-8}$ | 17.0 |
| H-Ala-Gly-Pro-CO-Benzothiazole*TFA | $1.07*10^{-7}$ | 5.1 |
| H-Ala-Val-Pro-CO-Thiazole*TFA | $3.32*10^{-8}$ | 15.1 |
| H-Ala Val-Pro-CO-(2-Pyridinyl)*TFA | n.d. | n.d. |
| H-Ala-Val-Pro-CO—$CH_2$—S—$CH_2$-Dichlorophenyl*TFA | $<1.0*10^{-7}$ | n.d. | n.d. not determined

Example 3

Determination of $IC_{50}$-Values

100 µl inhibitor stock solution was mixed with 100 µl buffer (HEPES pH7.6) and 20 µl diluted porcine DPIV and preincubated at 30° C. Reaction was started by addition of a mixture of 50 µl substrate (Gly-Pro-pNA, final concentration 0.4 mM) and 2 µl APN stock solution. Formation of the product pNA was measured at 405 nm and 30° C. over 10 min using the HTS 7000Plus plate reader (Perkin Elmer) and slopes were calculated. The final inhibitor concentrations ranged between 1 mM and 30 nM. For calculation of $IC_{50}$ GraFit 4.0.13 (Erithacus Software) was used.

3.1 Results-Determination of $IC_{50}$ Values

| Compound | $IC_{50}$ [M] |
| --- | --- |
| H-Ala-Val-Pro-Me*HBr | $5.79*10^{-7}$ |
| H-Val-Pro-Val-Pro-Me*HBr (SEQ ID NO:1) | n.d. |
| H-Ala-Val-Pro-CH$_2$O—CO—CH$_3$*HBr | $1.02*10^{-8}$ |
| H-Ala-Val-Pro-CO—CH$_2$O—CO—Ph*HBr | $1.79*10^{8}$ |
| H-Gly-Val-Pro-CO—CH$_2$O—CO—Ph*HBr | $4.94*10^{-6}$ |
| H-Ala-Val-Pro-CO-Benzothiazole*TFA | n.d. |
| H-Ala-Gly-Pro-CO-Benzothiazole*TFA | n.d. |
| H-Ala-Val-Pro-CO-Thiazole*TFA | no inhibition |
| H-Ala Val-Pro-CO-(2-Pyridinyl)*TFA | $1.10*10^{-3}$ |
| H-Ala-Val-Pro-CO—CH$_2$—S—CH$_2$-Dichlorophenyl*TFA | $7.97*10^{-5}$ | n.d. not determined

Example 4

Inhibition of DPIV-Like Enzymes-Dipeptidyl Peptidase II (DP II)

DP II (3.4.14.2) releases N-terminal dipeptides from oligopeptides if the N-terminus is not protonated (McDonald, J. K., Ellis, S. & Reilly, T. J., 1966, J. Biol. Chem., 241, 1494-1501). Pro and Ala in P1-position are preferred residues. The enzyme activity is described as DPIV-like activity, but DP II has an acidic pH-optimum. The enzyme used was purified from porcine kidney.

Assay:

100 µl inhibitor in a concentration range of $1*10^{-4}$ M-$5*10^{-8}$ M was admixed with 100 µl buffer solution (40 mM HEPES, pH7.6, 0.015% Brij, 1 mM DTT), 50 µl lysyla-lanylaminomethylcoumarine solution (5 mM) and 20 µl porcine DP II (250fold diluted in buffer solution). Fluorescence measurement was performed at 30° C. and $\lambda_{excitation}$=380 nm, $\lambda_{emission}$=465 nm for 25 min using a plate reader (HTS7000plus, Applied Biosystems, Weiterstadt, Germany). The $K_i$-values were calculated using Graphit 4.0.15 (Erithacus Software, Ltd., UK).

Results:

The compound H-Ala-Val-Pro-CO—CH$_2$O—CO-Ph*HBr was exemplarily tested against DP II. No inhibition of DP II by H-Ala-Val-Pro-CO—CH$_2$O—CO-Ph*HBr was found.

Attractin

100 µl inhibitor stock solution was mixed with 100 µl buffer (HEPES pH7.6) and 20 µl diluted attractin and preincubated at 30° C. Reaction was started by addition of a mixture of 50 µl substrate (Gly-Pro-pNA, final concentration 0.4 mM) and 2 µl APN stock solution. Formation of the product pNA was measured at 405 nm and 30° C. over 10 min using the HTS 7000Plus plate reader (Perkin Elmer) and slopes were calculated. The final inhibitor concentrations ranged between 1 mM and 30 nM. For calculation of $IC_{50}$ values, GraFit 4.0.13 (Erithacus Software) was used.

Results:

The compound H-Ala-Val-Pro-Me*HBr was exemplarily tested against attractin. No inhibition of attractin by H-Ala-Val-Pro-Me*HBr was found.

Example 5

Cross Reacting Enzymes

The inhibitors were tested for their cross reacting potency against dipeptidyl peptidase I, prolyl oligopeptidase and Prolidase.

Dipeptidyl peptidase I (DP I, cathepsin C):

DP I or cathepsin C is a lysosomal cysteine protease which cleaves off dipeptides from the N-terminus of their substrates (Gutman, H. R. & Fruton, J. S., 1948, J. Biol: Chem., 174, 851-858). It is classified as a cysteine protease. The enzyme used was purchased from Qiagen (Qiagen GmbH, Hilden, Germany). In order to get a fully active enzyme, the enzyme was diluted 1000 fold in MES buffer pH5.6 (40 mM MES, 4 mM DTT, 4 mM KCl, 2 mM EDTA, 0.015% Brij) and pre-incubated for 30 min at 30° C.

Assay:

50 µl solution with the test compounds in a concentration range of $1*10^{-5}$ M-$1*10^{-7}$ M was admixed with 110 µl buffer-enzyme-mixture. The assay mixture was pre-incubated at 30° C. for 15 min. After pre-incubation, 100 µl histidylseryl-βnitroaniline ($2*10^{-5}$M) was added and measurement of yellow color development due to β-nitroaniline release was performed at 30° C. and $\lambda_{excitation}$=380 nm, $\lambda_{emission}$=465 nm for 10 min, using a plate reader (HTS7000 plus, Applied Biosystems, Weiterstadt, Germany).

The IC$_{50}$-values were calculated using Graphit 4.0.15 (Erithacus Software, Ltd., UK).

Prolidase (X-Pro dipeptidase)

Prolidase (EC 3.4.13.9) was first described by Bergmann & Fruton (Bergmann, M. & Fruton, J S, 1937, *J. Biol. Chem.* 189-202). Prolidase releases the N-terminal amino acid from Xaa-Pro dipeptides and has a pH optimum between 6 and 9.

Prolidase from porcine kidney (ICN Biomedicals, Eschwege, Germany) was solved (1 mg/ml) in assay buffer (20 mM NH$_4$(CH3COO)$_2$, 3 mM MnCl$_2$, pH 7.6). In order to get a fully active enzyme the solution was incubated for 60 min at room temperature.

Assay:

450 µl solution with the test compounds in an concentration range of $5*10^{-3}$ M-$5*10^{-7}$ M were admixed with 500 µl buffer solution (20 mM NH$_4$(CH$_3$COO)$_2$, pH 7.6) and 250 µl Ile-Pro-OH (0.5 mM in the assay mixture). The assay mixture was pre-incubated at 30° C. for 5 min. After pre-incubation, 75 µl Prolidase (1:10 diluted in assay buffer) was added and measurement was performed at 30° C. and λ=220 nm for 20 min using a UV/Vis photometer, UV1 (Thermo Spectromc, Cambridge, UK).

The IC 50-values were calculated using Graphit 4.0.15 (Erithacus Software, Ltd., UK).

Angiotensin-I Converting Enzyme (ACE)

Angiotensin I-converting enzyme (ACE; peptidyl-dipeptidase A) is a zinc metallopeptidase which cleaves the C-terminal dipeptide from angiotensin I to produce the potent vasopressor octapeptide angiotensin II (Skeggs, L. T., Kahn, J. R. & Shumway, N. P. (1956) The preparation and function of the hypertensin-converting enzyme. J. Exp. Med. 103, 295-299.) and inactivates bradykinin by the sequential removal of two C-terminal dipeptides (Yang, H. Y. T., Erdös, E. G. & Levin, Y. (1970) A dipeptidyl carboxypeptidase that converts angiotensin I and inactivates bradykinin. Biochim. Biophys. Acta 214, 374-376.). In addition to these two main physiological substrates, which are involved in blood pressure regulation and water and salt metabolism, ACE cleaves C-terminal dipeptides from various oligopeptides with a free C-terminus. ACE is also able to cleave a C-terminal dipeptide amide.

Assay:

C. for 15 min. After pre-incubation, 50 µl Acetyl-Met-AMC solution (0.54 mM) was added. Release of the AMC was measured at 30° C. using a NOVOstar fluorescence microplate reader (BMG) and excitation/emission wavelengths of 380/460 nm.

The $IC_{50}$-values were calculated from the slopes of the progress curves using Graphit 4.0.15 (Erithacus Software, Ltd., UK).

5.1 Results—Determination of $IC_{50}$ Values against Cross-Reacting Enzymes

| Compound | DP I $IC_{50}[M]$ | Prolidase $IC_{50}[M]$ | ACE $IC_{50}[M]$ | AARE $IC_{50}[M]$ |
|---|---|---|---|---|
| H-Ala-Val-Pro-Me*HBr | no inhibition | $4.13*10^{-4}$ | no inhibition | no inhibition |
| H-Ala-Val-Pro-$CH_2O$—CO—$CH_3$*HBr | $1.20*10^{-4}$ | no inhibition | no inhibition | no inhibition |
| H-Ala-Val-Pro-CO—$CH_2O$—CO—Ph*HBr | $3.16*10^{-4}$ | $4.14*10^{-4}$ | no inhibition | no inhibition |

For $IC_{50}$ determination of ACE an enzyme produced by Sigma was used (Prod. No. A-6778). The assay procedure and calculation of activity described by the manufacturer was adapted to half of the described volumes.

The $IC_{50}$-values were calculated using Graphit 4.0.15 (Erithacus Software, Ltd., UK).

Acylamino Acid-Releasing Enzyme (AARE)

Acylaminoacyl-peptidase (EC 3.4.19.1) has also been referred to by the names acylpeptide hydrolase (Gade, W. & Brown, J. L. (1978) Purification and partial characterization of a-N-acylpeptide hydrolase from bovine liver. J. Biol. Chem. 253, 5012-5018.; Jones, W. M. & Manning, J. M. (1985) Acylpeptide hydrolase activity from erythrocytes. Biochem. Biophys. Res. Commun. 126, 933-940; Koba-Yashi, K., Lin, L.-W., Yeadon, J. E., Klickstein, L. B. & Smith, J. A. (1989) Cloning and sequence analysis of a rat liver cDNA encoding acylpeptide hydrolase. J. Biol. Chem. 264, 8892-8899), acylamino acid-releasing enzyme (Tsunasawa, S., Narita, K. & Ogata, K. (1975) Purification and properties of acylamino acid-releasing enzyme from rat liver. J. Biochem. 77, 89-102; Mitta, M., Asada, K., Uchimura, Y., Kimizuka, F., Kato, I., Sakiyama, F. & Tsunasawa, S. (1989) The primary structure of porcine liver acylamino acid-releasing enzyme deduced from cDNA sequences. J. Biochem. 106, 548-551.) and acylaminoacyl peptide hydrolase (Radhakrishna, G. & Wold, F. (1989) Purification and characterization of an N-acylaminoacyl-peptide hydrolase from rabbit muscle. J. Biol. Chem. 264, 11076-11081.). Acylaminoacyl peptidase catalyzes the removal of an N-acylated amino acid from a blocked peptide: Block-Xaa↓Xbb-Xcc . . . . The products of the reaction are the free acyl amino acid and a peptide with a free N-terminus shortened by one amino acid. The enzyme acts on a variety of peptides with different N-terminal acyl groups, including acetyl, chloroacetyl, formyl and carbamyl (Jones, W. M., Scaloni, A., Bossa, F., Popowicz, A. M., Schneewind, O. & Manning, J. M. (1991) Genetic relationship between acylpeptide hydrolase and acylase, two hydrolytic enzymes with similar binding but different catalytic specificities. Proc. Natl. Acad. Sci. USA 88, 2194-2198.).

Assay:

100 µl solution with the inhibitors in a concentration range of $1*10^{-4}$ M-$5*10^{-8}$ M were admixed with 100 µl µl buffer solution (200 mM sodium phosphate, pH 7.2) and 20 µl AARE solution. The assay mixture was pre-incubated at 30°

Example 6

Determination of DPIV Inhibiting Activity After Intravasal and Oral Administration to Wistar Rats Animals Male Wistar rats (Shoe: Wist(Sho)) with a body weight ranging between 250 and 350 g were purchased from Tierzucht Schönwalde (Schönwalde, Germany).

Housing Conditions

Animals were single-caged under conventional conditions with controlled temperature (22±2° C.) on a 12/12 hours light/dark cycle (light on at 06:00 AM). Standard pelleted chow (ssniff® Soest, Germany) and tap water acidified with HCl were allowed ad libitum.

Catheter Insertion into Carotid Artery

After ≧one week of adaptation at the housing conditions, catheters were implanted into the carotid artery of Wistar rats under general anaesthesia (i.p. injection of 0.25 ml/kg b.w. ROMPUN® [2%], BayerVital, Germany and 0.5 ml/kg b.w. Ketamin 10, Atarost GmbH & Co., Twistringen, Germany). The animals were allowed to recover for one week. The catheters were flushed with heparin-saline (100 IU/ml) three times per week. In case of catheter dysfunction, a second catheter was inserted into the contralateral carotid artery of the respective rat. After one week of recovery from surgery, this animal was reintegrated into the study. In case of dysfunction of the second catheter, the animal was withdrawn from the study. A new animal was recruited and the experiments were continued in the planned sequence, beginning at least 7 days after catheter implantation.

Experimental Design

Rats with intact catheter function were administered placebo (1 ml saline, 0.154 mol/l) or test compound via the oral and the intra-vasal (intra-arterial) route. After overnight fasting, 100 µl samples of heparinised arterial blood were collected at -30, -5, and 0 min. The test substance was dissolved freshly in 1.0 ml saline (0.154 mol/l) and was administered at 0 min either orally via a feeding tube (75 mm; Fine Science Tools, Heidelberg, Germany) or via the intra-vasal route. In the case of oral administration, an additional volume of 1 ml saline was injected into the arterial catheter. In the case of intra-arterial administration, the catheter was immediately flushed with 30 μl saline and an additional 1 ml of saline was given orally via the feeding tube.

After application of placebo or the test substances, arterial blood samples were taken at 2.5, 5, 7.5, 10, 15, 20, 40, 60 and 120 min from the carotid catheter of the conscious unrestrained rats. All blood samples were collected into ice cooled Eppendorf tubes (Eppendorf-Netheler-Hinz, Hamburg, Germany) filled with 10 μl 1M sodium citrate buffer (pH 3.0) for plasma DPIV activity measurement. Eppendorf tubes were centrifuged immediately (12000 rpm for 2 min, Hettich Zentrifuge EBA 12, Tuttlingen; Germany): The plasma fractions were stored on ice until analysis or were frozen at −20° C. until analysis. All plasma samples were labelled with the following data:

Code number

Animal Number

Date of sampling

Time of sampling

Analytical Methods

The assay mixture for determination of plasma DPIV activity consisted of 80 μl reagent and 20 μl plasma sample. Kinetic measurement of the formation of the yellow product 4-nitroaniline from the substrate glycylprolyl-4-nitroaniline was performed at 390 nm for 1 min at 30° C. after 2 min pre-incubation at the same temperature. The DPIV activity was expressed in mU/ml.

Statistical Methods

Statistical evaluations and graphics were performed with PRISM® 3.02 (GraphPad Software, Inc.). All parameters were analysed in a descriptive manner including mean and SD.

6.1 Results—In Vivo DPIV-Inhibition at $t_{max}$

| Compound | Dose (mg/kg) | i.v. (%) | p.o. (%) |
|---|---|---|---|
| H-Ala-Val-Pro-CH$_2$O—CO—CH$_3$*HBr | 100 | 89 | 87 |
| H-Ala-Val-Pro-CO—CH$_2$O—CO—Ph*HBr | 100 | 95 | 68 |

Example 7

The effect of Substituted Amino Ketones on Glucose Tolerance in Diabetic Zucker Rats Study Design Animals N=30 male Zucker rats (fa/fa), mean age 11 weeks (5-12 weeks), mean body weight 350 g (150-400 g), were purchased from Charles River (Sulzfeld, Germany). They were kept for >12 weeks until all the fatty Zucker rats had the characteristics of manifest Diabetes mellitus.

Housing Conditions

Animals were kept single-housed under conventional conditions with controlled temperature (22±2° C.) on a 12/12 hours light/dark cycle (light on at 06:00 a.m.). Standard pellets (ssniff®, Soest, Germany) and tap water acidified with HCl were allowed ad libitum.

Catheterization of Carotid Artery

Fatty Zucker rats, 17-24 weeks old, adapted to the housing conditions, were well prepared for the tests. Catheters were implanted into the carotid artery of fatty Zucker rats under general anaesthesia (i.p. injection of 0.25 ml/kg b.w. Rompun® [2%], BayerVital, Germany and 0.5 ml/kg b.w. Ketamin 10, Atarost GmbH & Co., Twistringen, Germany). The animals were allowed to recover for one week. The catheters were flushed with heparin-saline (100 IU/ml) three times per week. In case of catheter dysfunction, a second catheter was inserted into the contra-lateral carotid artery of the respective rat. After one week of recovery from surgery, this animal was reintegrated into the study. In case of dysfunction of the second catheter, the animal was withdrawn from the study. A new animal was recruited and the experiments were continued in the planned sequence, beginning at least 7 days after catheter implantation.

Experimental Design

Fatty Zucker rats with intact catheter function were given in random order placebo (1 ml saline, 0.154 mol/l; N=9 animals as control), or test substance, solved in 1 ml saline (N=6 animals in each test group).

After overnight fasting, the fatty Zucker rats were given placebo and test substance, respectively, via feeding tube orally (15 G, 75 mm; Fine Science Tools, Heidelberg, Germany) at −10 min. An oral glucose tolerance test (OGTT) with 2 g/kg b.w. glucose as a 40% solution (B. Braun Melsungen, Melsungen, Germany) was implemented at ±0 min. The glucose was administered via a second feeding tube. Arterial blood samples from the carotid catheter were collected at −30 min, −15 min, ±0 min and at 5, 10, 15, 20, 30, 40, 60, 90 and 120 min into 20 μl glass capillaries, which were placed in standard tubes filled with 1 ml solution for hemolysis (blood glucose measurement).

In addition, arterial blood samples were taken at −30 min, at 20, 40 60 and 120 min from the carotid catheter of the conscious unrestrained fatty Zucker rats and given into ice cooled Eppendorf tubes (Eppendorf-Netheler-Hinz, Hamburg, Germany) filled with 10 μl sodium citrate buffer (pH 3.0) for plasma DP activity measurement. Eppendorf tubes were centrifuged immediately (12000 rpm for 2 min, Hettich Zentrifuge EBA 12, Tuttlingen; Germany): The plasma fractions were stored on ice until analysis.

Analytical Methods

Blood glucose: Glucose levels were measured using the glucose oxidase procedure (Super G Glukosemeßgerät; Dr. Müller Gerätebau, Freital, Germany).

The compounds of the present invention, tested in the in vivo assay, improved significantly the glucose tolerance after oral administration during an OGTT in Zucker rats (see 7.1).

7.1 Results—Improvement of Glucose Tolerance After Administration of Substituted Amino Ketones During an OGTT in Zucker Rats

| Compound | Dose (mg/kg b.w.) | Route of adm. | AUC Control (mmol*min/l) | AUC test compound (mmol*min/l) | Improvement (%) |
|---|---|---|---|---|---|
| H-Ala-Val-Pro-Me*HBr | 100 | oral | 766.2 | 394.4 | 48.5 |

-continued

| Compound | Dose (mg/kg b.w.) | Route of adm. | AUC Control (mmol*min/l) | AUC test compound (mmol*min/l) | Improvement (%) |
|---|---|---|---|---|---|
| H-Val-Pro-Val-Pro-Me*HBr[1] | 100 | oral | 118.8 | 66.4 | 44.1 |
| H-Ala-Val-Pro-CH$_2$O—CO—CH$_3$*HBr | 5 | oral | 561.5 | 309.1 | 44.9 |
| H-Ala-Val-Pro-CH$_2$O—CO—CH$_3$*HBr | 15 | oral | 561.5 | 300.9 | 46.4 |
| H-Ala-Val-Pro-CH$_2$O—CO—CH$_3$*HBr | 50 | oral | 561.5 | 254.7 | 54.6 |
| H-Ala-Val-Pro-CO—CH$_2$O—CO—Ph*HBr | 5 | oral | 517.3 | 209.1 | 59.5 |
| H-Ala-Val-Pro-CO—CH$_2$O—CO—Ph*HBr | 15 | oral | 517.3 | 245.4 | 52.6 |
| H-Ala-Val-Pro-CO—CH$_2$O—CO—Ph*HBr | 50 | oral | 517.3 | 160.5 | 69.0 |

[1]tested in Wistar rats under identical experimental conditions

It will be readily understood by those skilled in the art that the foregoing are merely exemplary and that numerous departures may be made without departing from the spirit or scope of the present invention.

What is claimed is:

1. A compound formula 1:

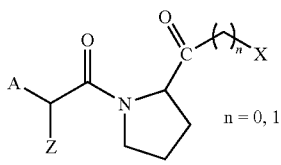

or a pharmaceutically acceptable salts thereof, wherein:

A is selected from:

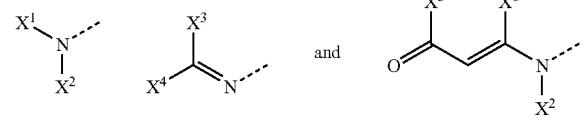

wherein $X^1$ is H or an amino acid residue, a N-protected amino acid residue, a peptide residue or a N-protected peptide residue, $X^2$ is H, —(CH)$_m$—NH—C$_5$H$_3$N—Y with m=2-4, or —C$_5$H$_3$N—Y (a divalent pyridyl residue) and Y is selected from H, Br, Cl, I, NO$_2$ and CN, $X^3$ is H or an alkyl-, alkoxy-, halogen-, nitro-, cyano- or carboxy-substituted phenyl or from an alkyl-, alkoxy-, halogen-, nitro-, cyano- or carboxy-substituted pyridyl residue, $X^4$ is H or an alkyl-, alkoxy-, halogen-, nitro-, cyano- or carboxy-substituted phenyl or an alkyl-, alkoxy-, halogen-, nitro-, cyano- or carboxy-substituted pyridyl residue, $X^5$ is H or an alkyl, alkoxy or phenyl residue, $X^6$ is H or an alkyl residue, for n=1

X is selected from OR$^2$ and SR$^2$, wherein:

R$^2$ is an acyl residues, optionally substituted with alkyl, cycloalkyl, aryl or heteroaryl residues, or an amino acid residue or peptidic residue, or alkyl residue, which are optionally substituted with alkyl, cycloalkyl, aryl or heteroaryl residues, for n=0

X is selected from:

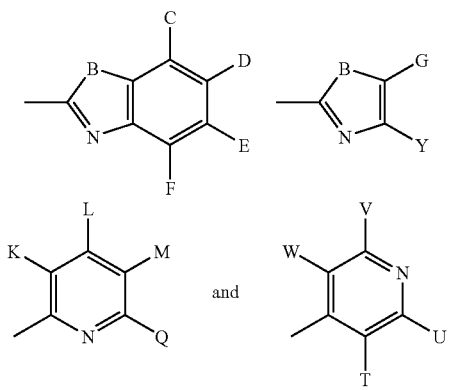

wherein
- B is O, S or NR$^5$, wherein R$^5$ is H, alkyl or acyl,
- C, D, E, F, G, Y, K, L, M, Q, T, U, V and W are independently selected from alkyl and substituted alkyl residues, oxyalkyl, thioalkyl, aminoalkyl, carbonylalkyl, acyl, carbamoyl, aryl and heteroaryl residues, and
- Z is H, or a branched or straight chain alkyl residue from $C_1$-$C_9$, a branched or straight chain alkenyl residue from $C_2$-$C_9$, a cycloalkyl residue from $C_3$-$C_8$, a cycloalkenyl residue from $C_5$-$C_7$, an aryl or heteroaryl residue, or a side chain selected from all side chains of all natural amino acids or derivatives thereof.

2. A compound selected from the group consisting of
2-methylcarbonyl-1-N-[(L)-Alanyl-(L)-Valinyl]-(2S)-pyrrolidine hydrobromide;
2-methylcarbonyl-1-N-[(L)-Valinyl-(L)-Prolyl-(L)-Valinyl]-(2S)-pyrrolidine hydrobromide;
2-[(acetyloxy-methyl)carbonyl]-1-N-[(L)-Alanyl-(L)-Valinyl]-(2S)-pyrrolidine hydrobromide;
2-[(benzoyloxy-methyl)carbonyl]-1-N-[{(L)-Alanyl}-(L)-Valinyl]-(2S) -pyrrolidine hydrobromide;
2-{[(2,6-dichlorobenzyl)thiomethyl]carbonyl}-1-N-[{(L)-Alanyl}-(L)-Valinyl]-(2S)-pyrrolidine;
2-[(benzoyloxy-methyl)carbonyl]-1-N-[Glycyl-(L)-Valinyl]-(2S)-pyrrolidine hydrobromide;
2-[([1,3]-thiazol-2-yl)carbonyl]-1-N-[{(L)-Alanyl}-(L)-Valinyl]-(2S)-pyrrolidine trifluoracetate;
2-[(benzothiazol-2-yl)carbonyl]-1-N-[{(L-Alanyl}-(L)-Valinyl]-(2S)-pyrrolidine trifluoracetate;
2-[(-benzothiazol-2-yl)carbonyl]-1-N-[{(L)-Alanyl}-Glycyl]-(2S)-pyrrolidine trifluoracetate; and
2-[(pyridin-2-yl)carbonyl]-1-N[{(L)-Alanyl}-(L)-Valinyl]-(2S)-pyrrolidine trifluoracetate.

3. A pharmaceutical composition for parenteral, enteral or oral administration, characterised in that it contains at least one compound according to claim 1 optionally in combination with customary carriers or excipients.

4. A compound according to claim 1 or a pharmaceutically acceptable salt thereof, wherein A is:

wherein
- X$^1$ is H or an amino acid residue, an N-acylated amino acid residue, a peptide residue from di- to pentapeptides, or an N-protected peptide residue from di- to pentapaptides,
- X$^2$ is H, —(CH)$_m$—NH—C$_5$H$_3$N—Y with m=2-4, or —C$_5$H$_3$N—Y (a divalent pyridyl residue) and Y is selected from H, Br, Cl, I, NO$_2$ and CN, for n=1
X is selected from OR$^2$ and SR$^2$, wherein:
- R$^2$ is an acyl residue, optionally substituted with alkyl, cycloalkyl, aryl or heteroaryl residues, or an amino acid residue or peptidic residue, or alkyl residue, optionally substituted with alkyl, cycloalkyl, aryl or heteroaryl residues, for n=0
X is selected from:

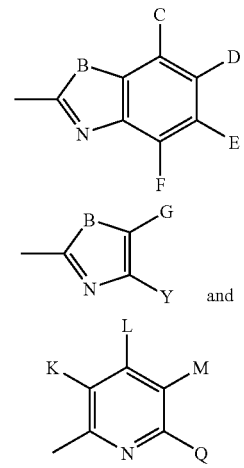

wherein
- B is O, S or NR$^5$, wherein R$^5$ is H, alkyl or acyl,
- C, D, E, F, G, Y, K, L, M and Q are independently selected from alkyl and substituted alkyl residues, oxyalkyl, thioalkyl, aminoalkyl, carbonylalkyl, acyl, carbamoyl, aryl and heteroaryl residues; and
- Z is H, or a branched or straight chain alkyl residue from $C_1$-$C_9$, a branched or straight chain alkenyl residue from $C_2$-$C_9$, a cycloalkyl residue from $C_3$-$C_8$, a cycloalkenyl residue from $C_5$-$C_7$, an aryl or heteroaryl residue, or a side chain selected from all side chains of all natural amino acids or derivatives thereof.

5. A compound of formula 1:

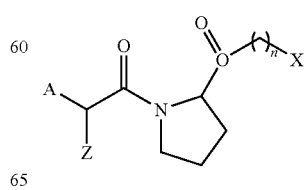

or a pharmaceutically acceptable salt thereof, wherein A is:

wherein
n=0

X¹ is H or an amino acid residue, an N-acylated amino acid residue, or a dipeptide residue containing a Pro or Ala in the penultimate position, or an N-protected dipeptide residue containing a Pro or Ala in the penultimate position, X is selected from:

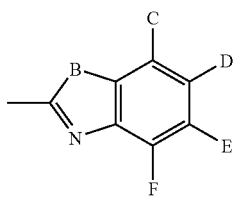

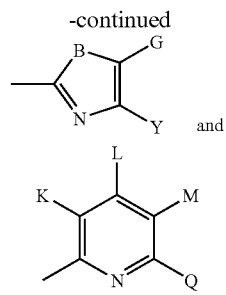

and wherein

B is O, C, D, E, F, G, Y, K, L, M and Q are H,

Z is H, or a branched or straight chain alkyl residue from $C_3$-$C_5$, a branched or straight chain alkenyl residue from $C_2$-$C_9$, a cycloalkyl residue from $C_5$-$C_7$, a cycloalkenyl residue from $C_5$-$C_7$, an aryl or heteroaryl residue, or a side chain selected from all side chains of all natural amino acids or derivatives thereof.

* * * * *

UNITED STATES PATENT AND TRADEMARK OFFICE
CERTIFICATE OF CORRECTION

PATENT NO. : 7,608,577 B2  Page 1 of 1
APPLICATION NO. : 10/216305
DATED : October 27, 2009
INVENTOR(S) : Heiser et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 847 days.

Signed and Sealed this

Twelfth Day of October, 2010

David J. Kappos
*Director of the United States Patent and Trademark Office*